US010445578B2

(12) United States Patent
Kudo

(10) Patent No.: US 10,445,578 B2
(45) Date of Patent: Oct. 15, 2019

(54) PHYSIOLOGICAL SENSOR CONTROLLER, PHYSIOLOGICAL SENSOR SYSTEM AND NON-TRANSITORY COMPUTER READABLE MEDIUM

(71) Applicant: FUJIFILM Corporation, Tokyo (JP)

(72) Inventor: Yuya Kudo, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 150 days.

(21) Appl. No.: 15/466,234

(22) Filed: Mar. 22, 2017

(65) Prior Publication Data
US 2017/0277962 A1    Sep. 28, 2017

(30) Foreign Application Priority Data

Mar. 23, 2016  (JP) ................................. 2016-058404

(51) Int. Cl.
| | |
|---|---|
| *G06K 9/00* | (2006.01) |
| *G16H 40/67* | (2018.01) |
| *G16H 40/40* | (2018.01) |
| *A61B 5/00* | (2006.01) |
| *A61B 5/0402* | (2006.01) |

(Continued)

(52) U.S. Cl.
CPC ........ *G06K 9/00671* (2013.01); *A61B 5/0002* (2013.01); *A61B 5/0022* (2013.01); *A61B 5/0402* (2013.01); *A61B 5/1176* (2013.01); *G06F 19/3418* (2013.01); *G06K 9/00892* (2013.01); *G16H 40/40* (2018.01); *G16H 40/67* (2018.01); *A61B 2562/08* (2013.01);
(Continued)

(58) Field of Classification Search
None
See application file for complete search history.

(56) References Cited

U.S. PATENT DOCUMENTS

| | | | | |
|---|---|---|---|---|
| 6,909,793 B1* | 6/2005 | Mori | .................. | A61B 5/02055 382/128 |
| 2011/0098086 A1* | 4/2011 | Nagata | .................... | H04M 1/21 455/557 |

(Continued)

FOREIGN PATENT DOCUMENTS

JP    2013-192859 A    9/2013

*Primary Examiner* — Kim Y Vu
*Assistant Examiner* — Nathan J Bloom
(74) *Attorney, Agent, or Firm* — Birch, Stewart, Kolasch & Birch, LLP

(57) ABSTRACT

A physiological sensor controller controls a physiological sensor (or ECG sensor), positioned on a patient body, for measuring physiological information (or ECG waveform) of the patient body to output a measurement signal. An acquisition device acquires a verification image containing portions of identification information of the physiological sensor and a face of the patient body. A verifier performs verification of acceptability in a combination of the physiological sensor and the patient body according to the verification image. A receiver receives the measurement signal. A detector detects normality or abnormality of receptivity of the measurement signal. A checker operates assuming that the detector determines the abnormality of the receptivity, and checks whether a retry for the verification in the verifier is required or not. An output device operates assuming that the checker determines requirement of the retry for the verification, and outputs information of encouraging the retry for the verification.

17 Claims, 34 Drawing Sheets

(51) Int. Cl.
  *G06F 19/00* (2018.01)
  *A61B 5/1171* (2016.01)
(52) U.S. Cl.
  CPC ............... *G06K 9/00288* (2013.01); *G06K 2009/00939* (2013.01)

(56) References Cited

U.S. PATENT DOCUMENTS

| | | | | |
|---|---|---|---|---|
| 2011/0305376 | A1* | 12/2011 | Neff | G16H 40/20 382/128 |
| 2011/0306926 | A1* | 12/2011 | Woo | G06F 3/0488 604/65 |
| 2012/0218404 | A1* | 8/2012 | Buxton | H04N 7/183 348/121 |
| 2012/0330680 | A1* | 12/2012 | O'Larte | G06Q 50/22 705/3 |
| 2013/0252691 | A1* | 9/2013 | Alexopoulos | G07F 17/3206 463/17 |
| 2014/0012509 | A1* | 1/2014 | Barber | G06F 3/015 702/19 |
| 2014/0233788 | A1* | 8/2014 | Fox | G06F 19/3418 382/103 |
| 2014/0320677 | A1* | 10/2014 | Jarvenpaa | H04N 5/23203 348/207.11 |
| 2016/0246936 | A1* | 8/2016 | Kahn | G06Q 50/22 |

* cited by examiner

FIG. 39
| A | ↑ | 0° | 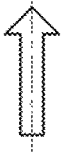 (ELECTRODE 102A, PAIR 103A) |
|---|---|---|---|
| B | ↗ | 45° | 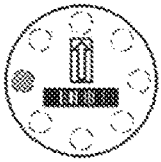 (ELECTRODE 102B, PAIR 103B) |
| C | → | 90° |  (ELECTRODE 102C, PAIR 103C) |
| D | ↘ | 135° |  (ELECTRODE 102D, PAIR 103D) |
| E | ↓ | 180° |  (ELECTRODE 102E, PAIR 103E) |
| F | ↙ | 225° |  (ELECTRODE 102F, PAIR 103F) |
| G | ← | 270° |  (ELECTRODE 102G, PAIR 103G) |
| H | ↖ | 315° |  (ELECTRODE 102H, PAIR 103H) |

2ND MESSAGE PAGE

No measurement signal is received
Turn on power supply for sensor
If battery is used up,
exchange battery

PHYSIOLOGICAL SENSOR CONTROLLER, PHYSIOLOGICAL SENSOR SYSTEM AND NON-TRANSITORY COMPUTER READABLE MEDIUM

CROSS-REFERENCE TO RELATED APPLICATION

This application claims priority under 35 USC 119 from Japanese Patent Application No. 2016-058404, filed 23 Mar. 2016, the disclosure of which is incorporated by reference herein.

BACKGROUND OF THE INVENTION

1. Field of the Invention

The present invention relates to a physiological sensor controller, a physiological sensor system and a non-transitory computer readable medium. More particularly, the present invention relates to a physiological sensor controller in which a combination between a physiological sensor and a patient can be verified in a facilitated manner without complexity, a physiological sensor system and a non-transitory computer readable medium.

2. Description Related to the Prior Art

In the field of medical instruments, a physiological sensor (physiological monitoring device) is used and positioned on a body of a patient (examinee) of home care at his or her home. A doctor (or other medical professionals) in a medical facility or hospital remotely monitors the patient's progress by use of the physiological sensor. The physiological sensor measures physiological information of the patient and outputs a measurement signal. Examples of the physiological information are a body temperature, blood pressure, heart rate, ECG (electrocardiogram), respiratory rate and the like. The measurement signal is transmitted to a physiological sensor controller (physiological monitoring apparatus) for controlling the physiological sensor.

In a physiological sensor system (patient monitoring system) including the physiological sensor and the physiological sensor controller, it is important to keep high reliability of the physiological information. It is necessary to perform verification of correctness in a combination between the physiological sensor and the patient, so as to prevent occurrence of impersonation of a stranger for the patient, mismatch between the disease of the patient and the type of the physiological sensor, and the like.

JP-A 2013-192859 discloses testing of alcohol information of a driver of a vehicle with a purpose of preventing a drunken driver from driving. An ID information of an alcohol sensor and a verification image of a face of the driver are acquired at the same time as a component of alcohol in the body of the driver is measured by the alcohol sensor. It is checked according to the verification image whether the driver is identified correctly and whether the alcohol sensor is a properly used type. It is possible to avoid the impersonation of a stranger for the driver, and avoid fraud in the testing by use of an improper product of the alcohol sensor different from the properly used type.

The patient (examinee) positions the physiological sensor from the medical facility to his or her body at home. For example, the patient with a heart disease positions the physiological sensor on the left chest area for measuring the heart rate, ECG (electrocardiogram) or the like. In general, the physiological sensor frequently becomes removed from the body temporarily for the reason of taking a bath or the like. The physiological sensor is positioned on the body newly during a period of the measurement for plural times.

In case the physiological sensor is removed, there occurs abnormality in receptivity of the measurement signal at the physiological sensor controller. A reason for the abnormality in the receptivity can be temporary removal of the physiological sensor at the time of bathing, and also can be an error in delivering the physiological sensor of a certain type to the patient. In order to cope with the occurrence of the abnormality in the receptivity, it is suggested to provide a function of performing a retry for verification between the patient and the physiological sensor.

An example of the abnormality in the receptivity of the measurement signal is instantaneous interruption of a communication path at a short time in addition to that due to the removal of the physiological sensor. For this example, there is no possibility of an error in delivery of the physiological sensor. The use of the retry for verification is not favorable on the side of the patient because of complexity.

Verification of a combination between the physiological sensor and the patient may be possible by use of the method in JP-A 2013-192859 and utilization of the ID information of the physiological sensor and information of the face of the patient. However, the verification requires additional steps of operation because of use of the verification image. According to the known techniques, there is no suggestion of reducing the complexity in relation to the retry for verification particularly for situations without requirement of the retry for verification.

SUMMARY OF THE INVENTION

In view of the foregoing problems, an object of the present invention is to provide a physiological sensor controller in which a combination between a physiological sensor and a patient can be verified in a facilitated manner without complexity, a physiological sensor system and a non-transitory computer readable medium.

In order to achieve the above and other objects and advantages of this invention, a physiological sensor controller for controlling a physiological sensor, positioned on a patient body, for measuring physiological information of the patient body to output a measurement signal, is provided. An acquisition device acquires a verification image containing portions of identification information of the physiological sensor and a face of the patient body. A verifier performs verification of acceptability in a combination of the physiological sensor and the patient body according to the verification image. A receiver receives the measurement signal. A detector detects normality or abnormality of receptivity of the measurement signal received by the receiver. A checker operates assuming that the detector determines the abnormality of the receptivity, and checks whether a retry for the verification in the verifier is required or not. An output device operates assuming that the checker determines requirement of the retry for the verification, and outputs information of encouraging the retry for the verification.

Preferably, the checker checks whether the retry for the verification is required according to a time duration of continuing detection of the abnormality of the receptivity.

Preferably, the checker checks whether the retry for the verification is required according to a result of comparison between a measurement signal before detecting the abnormality of the receptivity and a measurement signal after recovery to the normality of the receptivity.

Preferably, furthermore, a position detector detects a sensor position of the physiological sensor according to the verification image. Assuming that the sensor position detected by the position detector is incorrect, the output device outputs information of incorrectness of the sensor position.

Preferably, the information of the incorrectness of the sensor position includes information for guiding to the sensor position being correct.

Preferably, the position detector detects the sensor position according to a position relationship with a particular body part of the patient body in a portion of the verification image.

Preferably, furthermore, a direction detector detects a sensor direction of the physiological sensor.

Preferably, the physiological sensor includes a direction indicator for indicating the sensor direction. The acquisition device acquires the verification image containing a portion of the direction indicator. The direction detector detects the sensor direction according to the verification image.

In another preferred embodiment, the direction detector detects the sensor direction according to the measurement signal.

Preferably, furthermore, a corrector operates assuming that the sensor direction detected by the direction detector is not determined to be normal, and corrects the measurement signal to a measurement signal in a state of normality of the sensor direction.

In still another preferred embodiment, the physiological sensor includes pairs of positive and negative electrodes corresponding to plural sensor directions. Furthermore, a drive control unit activates the physiological sensor by selecting a suitable pair of positive and negative electrodes among the pairs according to the sensor direction detected by the direction detector.

Preferably, assuming that the receiver does not receive the measurement signal upon lapse of predetermined time after the verifier determines the acceptability in the combination, then the output device provides notification that maintenance access to the physiological sensor should be performed to resume outputting the measurement signal.

Preferably, furthermore, a power control unit operates assuming that the receiver does not receive the measurement signal upon lapse of predetermined time after the verifier determines the acceptability in the combination, and assuming that a power supply for the physiological sensor is turned off, and causes turn-on of the power supply in relation to the physiological sensor.

Preferably, the acquisition device acquires plural image frames of the verification image for use in one time of the verification.

Also, a non-transitory computer readable medium for storing a computer-executable program enabling execution of computer instructions to perform operations for controlling a physiological sensor, positioned on a patient body, for measuring physiological information of the patient body to output a measurement signal. The operations include acquiring a verification image containing portions of identification information of the physiological sensor and a face of the patient body. The operations include performing verification of acceptability in a combination of the physiological sensor and the patient body according to the verification image. The operations include receiving the measurement signal. The operations include detecting normality or abnormality of receptivity of the measurement signal received by the receiving operation. The operations include an operation of, assuming that the detecting operation determines the abnormality of the receptivity, checking whether a retry for the verification in the verification operation is required or not. The operations include an operation of, assuming that the checking operation determines requirement of the retry for the verification, outputting information of encouraging the retry for the verification.

Also, a physiological sensor system includes a physiological sensor, positioned on a patient body, for measuring physiological information of the patient body to output a measurement signal, and a physiological sensor controller for controlling the physiological sensor. In the physiological sensor system, the physiological sensor controller includes an acquisition device for acquiring a verification image containing portions of identification information of the physiological sensor and a face of the patient body. A verifier performs verification of acceptability in a combination of the physiological sensor and the patient body according to the verification image. A receiver receives the measurement signal. A detector detects normality or abnormality of receptivity of the measurement signal received by the receiver. A checker operates assuming that the detector determines the abnormality of the receptivity, and checks whether a retry for the verification in the verifier is required or not. An output device operates assuming that the checker determines requirement of the retry for the verification, and outputs information of encouraging the retry for the verification.

Consequently, a combination between a physiological sensor and a patient can be verified in a facilitated manner without complexity, because information of encouraging a retry for the verification can be output only at the time of requirement.

BRIEF DESCRIPTION OF THE DRAWINGS

The above objects and advantages of the present invention will become more apparent from the following detailed description when read in connection with the accompanying drawings, in which:

FIG. 39 is a table illustrating correlation between an angle and a control signal;

DETAILED DESCRIPTION OF THE PREFERRED EMBODIMENT(S) OF THE PRESENT INVENTION

[First Embodiment]

Figure 1:
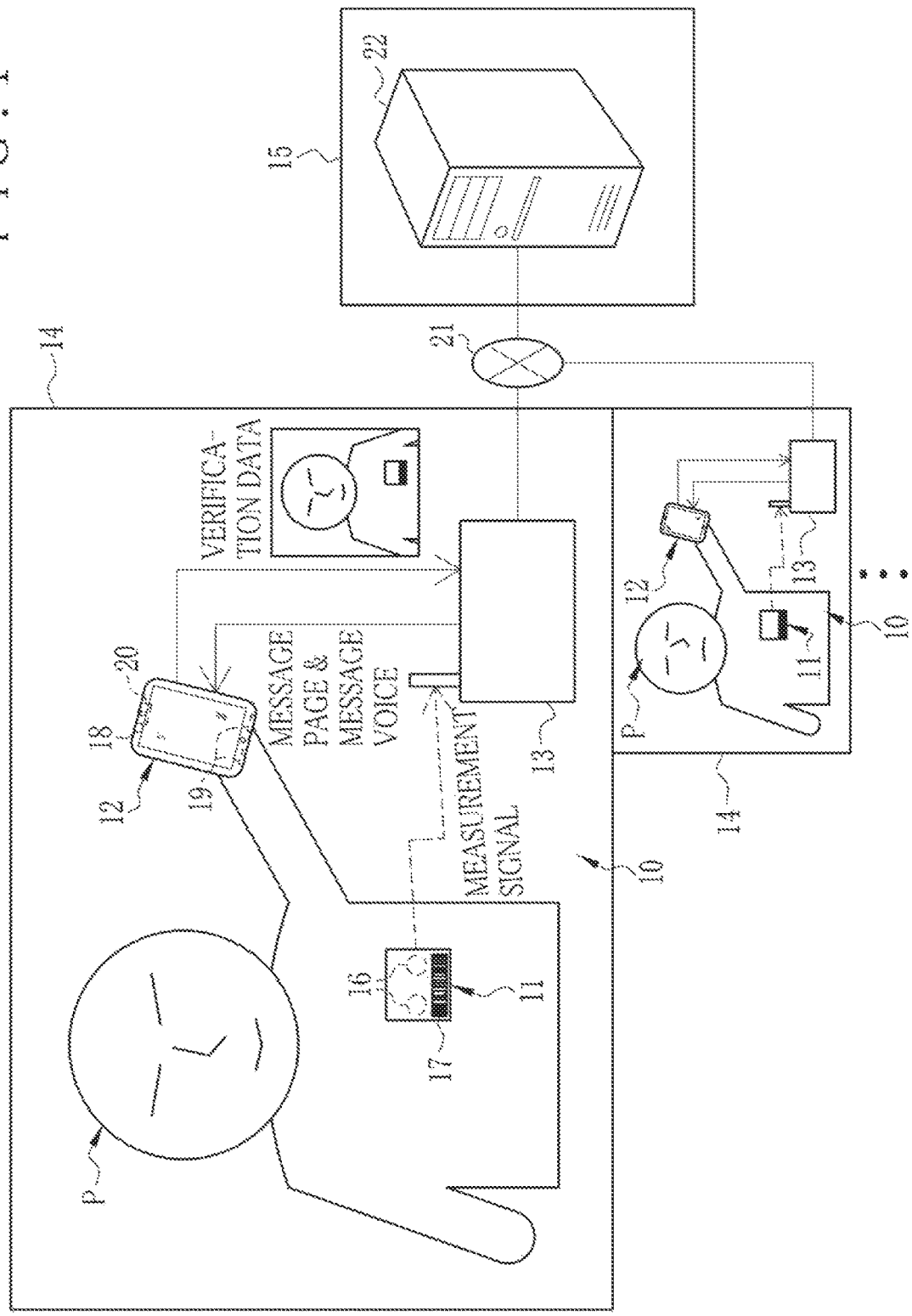
FIG. 1 is a block diagram schematically illustrating a physiological sensor system.

In FIG. 1, a physiological sensor system 10 (patient monitoring system) includes a physiological sensor 11 or ECG sensor (physiological monitoring device), and a physiological sensor controller 13 (physiological monitoring apparatus), and is installed in a patient's home 14 of a patient P (examinee) who uses a client terminal device 12. The patient P visits a medical facility 15 or hospital periodically as an out-patient. In the home 14, the patient P positions the physiological sensor 11 delivered by the medical facility 15 on his or her body.

The physiological sensor 11 measures physiological information of the patient P, and outputs a measurement signal at a predetermined sampling period. In the embodiment, a disease of the patient P is a heart disease. The physiological sensor 11 is an ECG sensor in a form of a regular square. The physiological information measured by the physiological sensor 11 is an ECG waveform. A measurement signal output by the physiological sensor 11 is a waveform signal of the ECG waveform.

The physiological sensor 11 is set on a left chest area of the patient P by use of an adhesive tape or the like. Plural electrodes 16 are incorporated in the physiological sensor 11 for measuring a waveform of an ECG (electrocardiogram). Also, a bar code 17 is disposed on the physiological sensor 11 for expressing a sensor ID (identification information) or particular information (such as property information) for recognizing the physiological sensor 11. An example of the bar code 17 is a one-dimensional code. Also, the bar code 17 can be a two-dimensional code.

Figure 2:
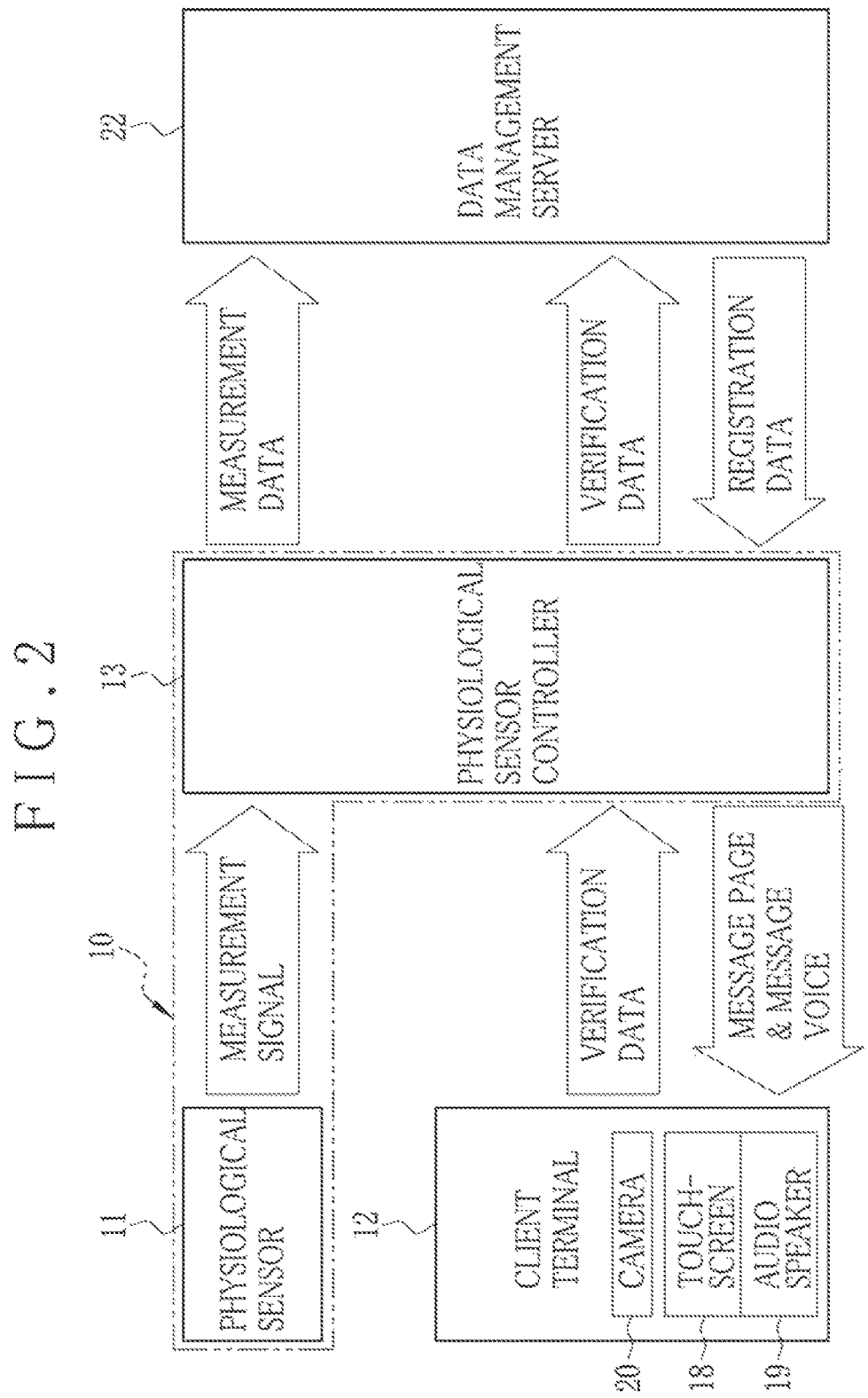
FIG. 2 is a block diagram schematically illustrating various data transmitted between a physiological sensor and a physiological sensor controller.

The physiological sensor 11 has a function of a short range radio communication interface for transmission and reception, for example, Bluetooth (trade name). In FIG. 2, the physiological sensor 11 wirelessly transmits a measurement signal to the physiological sensor controller 13 in a real-time manner as an output at a predetermined sampling period. Also, a battery is contained in the physiological sensor 11, to power the physiological sensor 11. It is possible to use the physiological sensor 11 in a wireless form.

Each of the client terminal device 12 and the physiological sensor controller 13 are constituted by installing computer-executable programs in a computer. Examples of the programs are a control program such as an operating system (OS), application programs (AP) of various types, and the like. Examples of the computer are a server computer, personal computer, workstation and the like.

An example of the client terminal device 12 is a smart phone used by the patient P, and includes a touchscreen device 18, an audio speaker 19 and a camera 20. The touchscreen device 18 displays various pages or screens according to a manual operation of the patient P. Each of the pages or screens has an operable function according to the GUI (graphical user interface). The client terminal device 12 receives a user input of the patient P through the page for a command signal. The audio speaker 19 outputs various sounds or voices. The camera 20 forms an image in response to a manual input for imaging by the patient P.

The client terminal device 12 and the physiological sensor controller 13 are interconnected in a communicable manner by use of a network (not shown), for example, LAN (local area network) installed in the home 14. In FIG. 2, the client terminal device 12 sends verification data of FIG. 4 to the physiological sensor controller 13 inclusive of a verification image for use in determining correctness in the combination of the physiological sensor 11 and the patient P after imaging with the camera 20. It is possible to connect the physiological sensor controller 13 with the client terminal device 12 by use of Bluetooth (trade name) or the like according to the short range radio communication.

The physiological sensor controller 13 controls the physiological sensor 11. The physiological sensor controller 13 performs verification to check acceptability in a combination of the physiological sensor 11 with the patient P to keep reliability of physiological information.

The physiological sensor controller 13 checks whether retry for verification of determining correctness in the combination between the physiological sensor 11 and the patient P is required. Assuming that it is judged that the retry for verification is required, a message is output to encourage the retry for verification as illustrated in FIG. 2.

Figure 14:
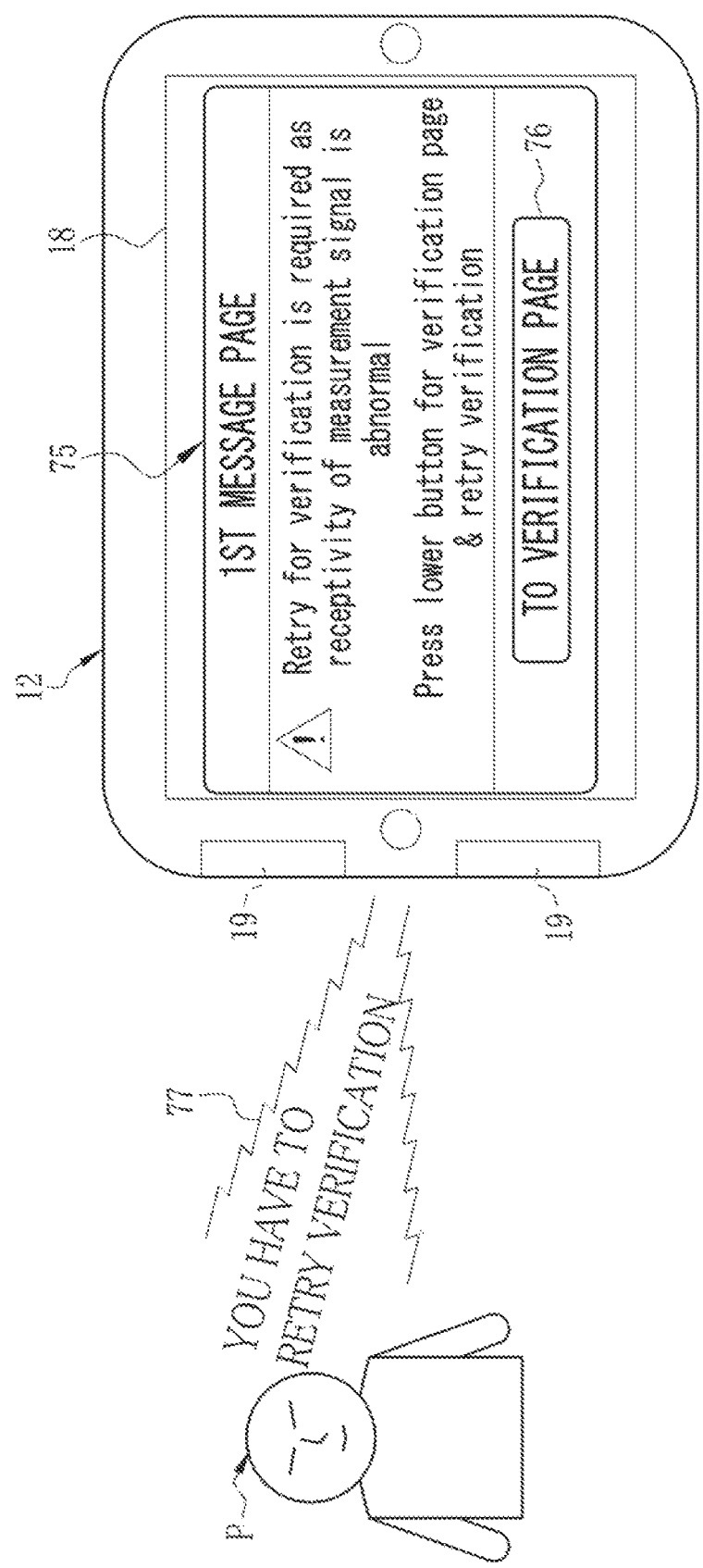
FIG. 14 is a screen view illustrating notification of encouraging the retry for the verification.

In the physiological sensor controller 13, a first message page 75 viewable with a web browser of the client terminal device 12 is created as illustrated in FIG. 14. The physiological sensor controller 13 outputs the first message page 75 to the client terminal device 12. Also, the physiological sensor controller 13 outputs a message voice 77 of FIG. 14 to the client terminal device 12 in a form of an output with the web browser.

The physiological sensor controller 13 outputs the first message page 75 in a format of XML data for web delivery created according to the XML (Extensible Markup Language) as a markup language. Also, it is possible to use another data description language instead of the XML, such as JSON (JavaScript Object Notation) and the like, JavaScript being a trade name. In addition to the first message page 75, the physiological sensor controller 13 outputs various pages or screens to the client terminal device 12 in a format of page data for web delivery.

The physiological sensor controller 13 is connected to a data management server 22 in a communicable manner by a network 21, namely the wide area network (WAN), such as the Internet, public communication network and the like. The data management server 22 is installed in the medical facility 15. Note that information security is established for use of the network 21, for example, the Virtual Private Network (VPN) or Hypertext Transfer Protocol Secure (HTTPS) is used as communication protocol of a high level of security.

The data management server 22 manages various data related to the physiological sensor system 10. Also, the data management server 22 outputs information of a graph with plotted measurement signals of a particular patient P in a time sequence to terminal devices of medical professionals, such as a personal computer and smart phone, and outputs alert information of an abrupt change of a condition of the patient P. It is possible remotely to monitor the condition of the patient P with the medical professionals in the medical facility 15 by use of the data management server 22 and the physiological sensor system 10.

In FIG. 2, the physiological sensor controller 13 produces measurement data according to the measurement signal from the physiological sensor 11 (see FIG. 3), and sends the measurement data to the data management server 22. Also, the physiological sensor controller 13 sends verification data from the client terminal device 12 to the data management server 22.

The data management server 22 stores and manages the measurement data from the physiological sensor controller 13 in a time sequence for the respective patient P. The data management server 22 also stores registration data for check with the verification data, and transmits the registration data to the physiological sensor controller 13.

Figure 3:
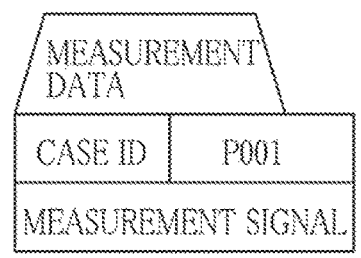
FIG. 3 is a data chart illustrating measurement data.
Figure 4:
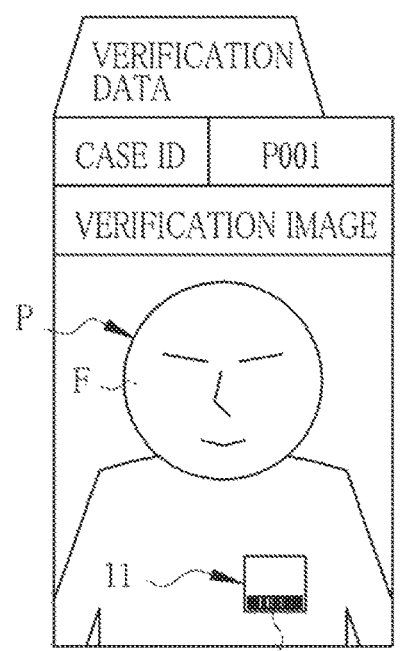
FIG. 4 is a data chart illustrating verification data.

In FIG. 3, the measurement data is constituted by the measurement signal and a case ID associated with the measurement signal for identification of the patient P. In FIG. 4, the verification data is constituted by the verification image and the case ID associated with the verification image. The verification image is constituted by the bar code 17 and a still image, the bar code 17 denoting a sensor ID of the physiological sensor 11, the still image containing a portion of a face F of the patient P. The camera 20 is used by the patient P to form the verification image.

Figure 5:
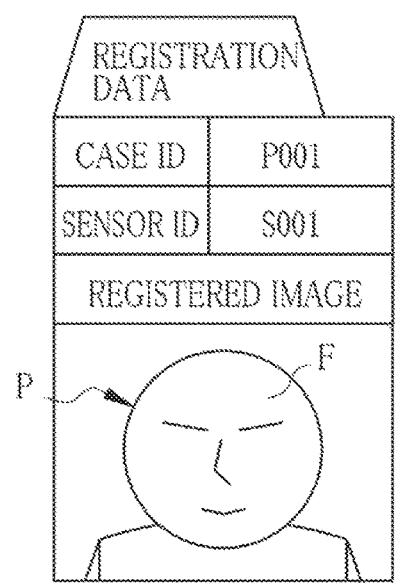
FIG. 5 is a data chart illustrating registration data.

In FIG. 5, the registration data is constituted by the case ID, sensor ID, and a registered image of a face F of the patient P. The registration data is produced by a medical professional at the same time as the physiological sensor 11 is delivered to the patient P in the medical facility 15, and written to the data management server 22. The data management server 22 stores various registration data for numerous patients P. The data management server 22 performs a search of the registration data of which the case ID is equal to a case ID of verification data (identification data) from the physiological sensor controller 13, and transmits the searched registration data to the physiological sensor controller 13.

Figure 6:
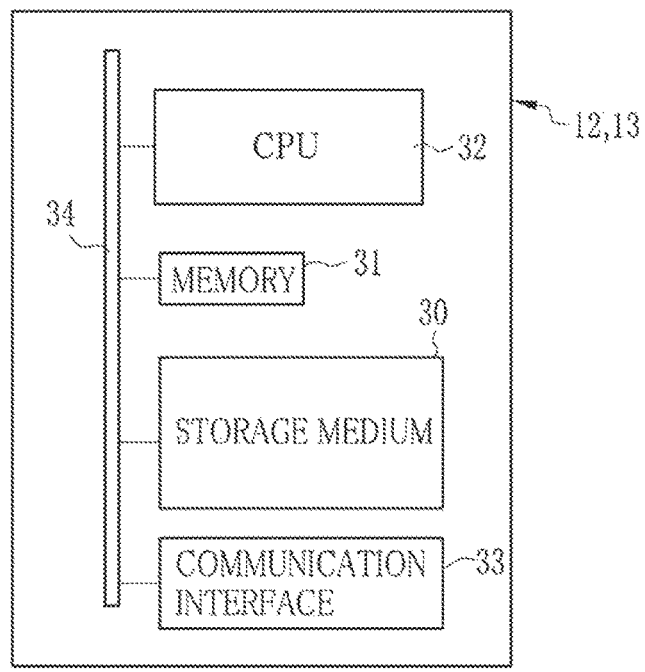
FIG. 6 is a block diagram schematically illustrating a computer apparatus constituting a client terminal device and a physiological sensor controller.

In FIG. 6, the client terminal device 12 and the physiological sensor controller 13 are constituted by computers of which structures are basically equal. Each computer has a storage medium 30 or storage device, a memory 31, a CPU 32 or central processing unit, and a communication interface 33. A data bus 34 interconnects those circuit devices.

The storage medium 30 is a hard disk drive incorporated in the computer constituting the client terminal device 12 and the like, or connected to the computer by a cable, network or the like. Also, the storage medium 30 may be a disk array having plural hard disk drives. The storage medium 30 stores a control program and various application programs such as the Operating System (OS), and various data associated with the programs.

The memory 31 is a working memory with which the CPU 32 performs tasks. The CPU 32 loads the memory 31 with the programs stored in the storage medium 30, and controls the various circuit devices in the computer by performing the tasks according to the program. The communication interface 33 is a network interface for control of transmission of various data by use of the network, for example, the LAN and WAN.

In the following description, a sign A will be added to each of reference signs of components in the computer constituting the client terminal device 12. A sign B will be added to each of reference signs of components in the computer constituting the physiological sensor controller 13.

Figure 7:
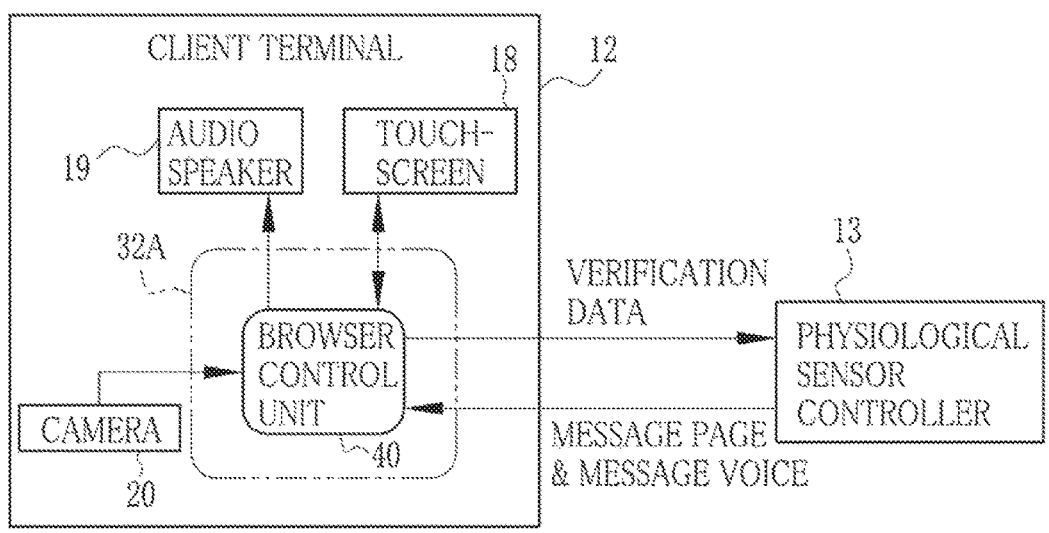
FIG. 7 is a block diagram schematically illustrating circuit devices in the client terminal device.

In FIG. 7, running the web browser causes a CPU 32A or central processing unit in the client terminal device 12 to establish a browser control unit 40 by cooperating with the memory 31 and the like.

The browser control unit 40 controls operation of the web browser. The browser control unit 40 receives page data of various pages including the first message page 75 from the physiological sensor controller 13. The browser control unit 40 produces the various pages for the web browser according to the page data, and drives the touchscreen device 18 to display the various pages. Also, the browser control unit 40 receives various control signals input by a medical professional with the touchscreen device 18 by use of the pages. Examples of the control signals include a signal for access to the physiological sensor controller 13, a signal for imaging of a verification image, and a signal for sending verification data. The browser control unit 40 issues a request to the physiological sensor controller 13 according to the control signals.

The browser control unit 40 receives information of various sounds and voices from the physiological sensor controller 13, inclusive of the message voice 77. The browser control unit 40 drives the audio speaker 19 to output the sounds and voices. Also, the browser control unit 40 receives a verification image from the camera 20, and creates verification data by adding the case ID to the verification image. The verification data is sent to the physiological sensor controller 13.

Figure 8:
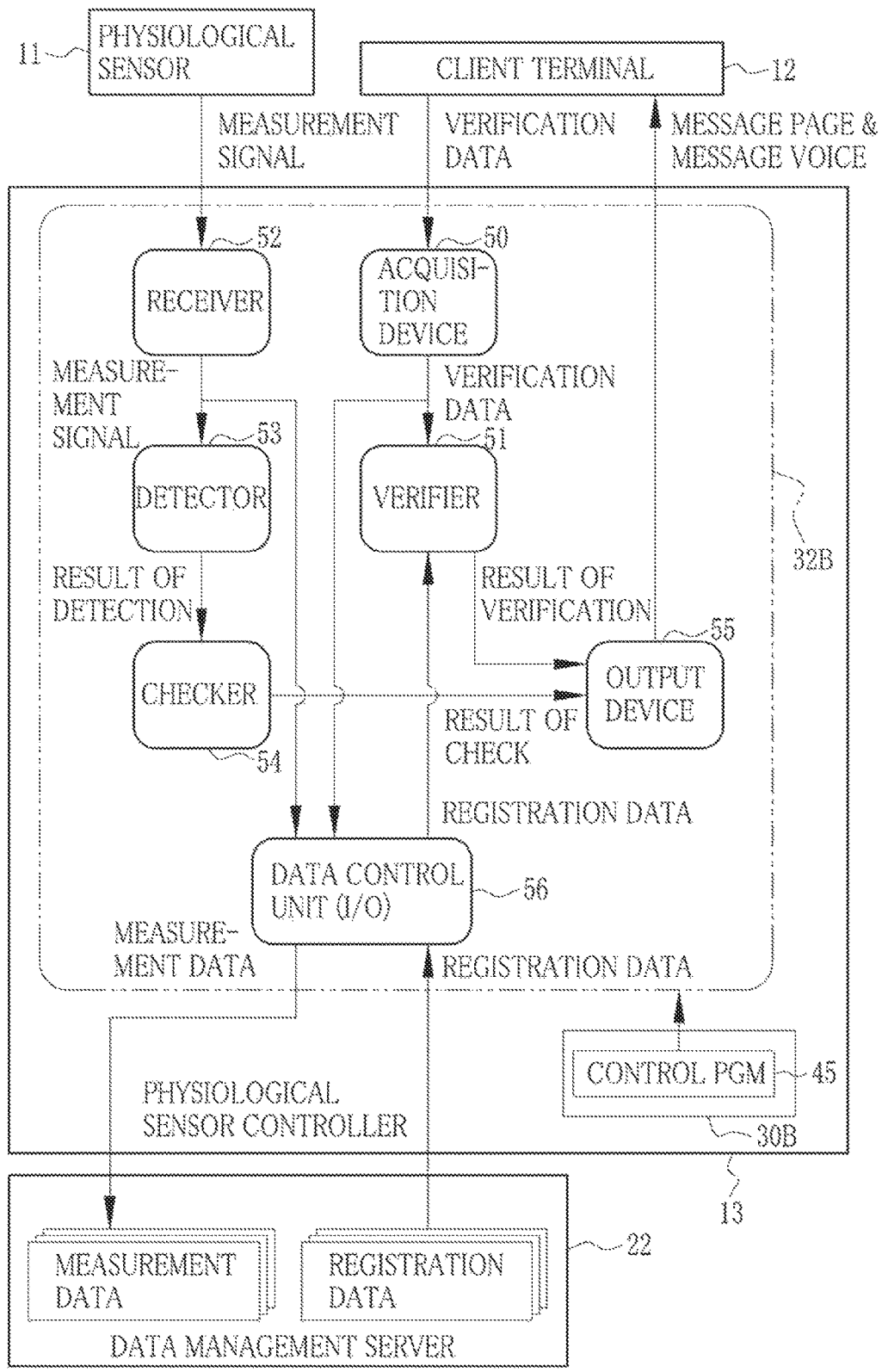
FIG. 8 is a block diagram schematically illustrating circuit devices in the physiological sensor controller.

In FIG. 8, a storage medium 30B or storage device in the physiological sensor controller 13 stores a control program 45 as application program. The control program 45 is used to run the computer to function as the physiological sensor controller 13.

Running the control program 45 in a CPU 32B or central processing unit in the physiological sensor controller 13 establishes various functional circuit devices in cooperation with the memory 31, inclusive of an acquisition device 50, a verifier 51, a receiver 52, a detector 53, a checker 54, an output device 55 (notification processor), and a data control unit 56 for inputs and outputs.

The acquisition device 50 acquires verification data from the client terminal device 12, namely, verification image. The acquisition device 50 outputs the verification data to the verifier 51 and the data control unit 56.

The verifier 51 performs verification of checking acceptability in a combination of the physiological sensor 11 with the patient P. The verifier 51 inputs a result of the verification to the output device 55.

The receiver 52 has a function of receiving the measurement signal from the data control unit 56. The receiver 52 inputs the measurement signal to the detector 53 and the data control unit 56.

The detector 53 checks normality of receptivity of the measurement signal. Assuming that the measurement signal from the receiver 52 discontinues for a predetermined time, the detector 53 detects abnormality of the receptivity of the measurement signal. Also, assuming that a signal level of the measurement signal from the receiver 52 continues not to be within a predetermined range for a predetermined time, the detector 53 detects abnormality of the receptivity of the measurement signal. In other cases, the detector 53 detects normality of the receptivity of the measurement signal. The detector 53 sets a result of the detection to the checker 54. An example of the predetermined time is from several milliseconds to several tens of milliseconds, namely, 5-10 times as long as the sampling period of the measurement signal.

The checker 54 checks whether the retry for verification in the verifier 51 is required or not assuming that the detector 53 detects abnormality of the receptivity. While the detector 53 determines normality of the receptivity, the checker 54 is inactive. The checker 54 sets a check result to the output device 55.

The output device 55 has a function of notifying the first message page 75 and the message voice 77 as messages for encouraging retry for verification assuming that the checker 54 determines requirement of the retry for verification. Also, the output device 55 outputs a verification page 60 of FIG. 9, result pages 70A and 70B for a verification result in FIGS. 11 and 12, and the like.

The data control unit 56 generates measurement data by adding the case ID to the measurement signal from the receiver 52, and outputs the measurement data to the data management server 22. The data control unit 56 transfers the registration data from the data management server 22 to the verifier 51.

Figure 9:
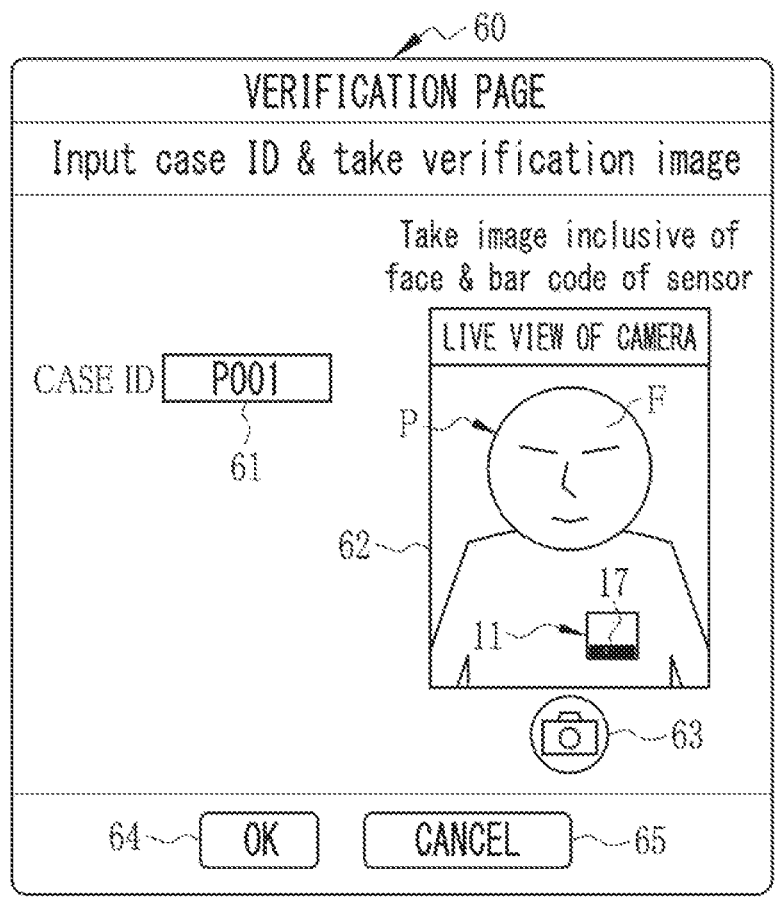
FIG. 9 is a screen view illustrating a verification page.

The output device 55 outputs the verification page 60 of FIG. 9 to the client terminal device 12. The verification page 60 includes an input box 61, a live view frame 62, a start button 63, an OK button 64 and a cancel button 65. The live view frame 62 is used for displaying a live image or live view of the camera 20. The input box 61 is used for inputting the case ID. The start button 63 is pressed for forming a verification image. Then the OK button 64 is pressed so that the client terminal device 12 sends verification data to the physiological sensor controller 13, the verification data being constituted by the case ID in the input box 61 and the verification image formed by use of the start button 63. Note that the case ID in the input box 61 is also associated with the measurement signal while the data control unit 56 produces the measurement data.

Figure 10:
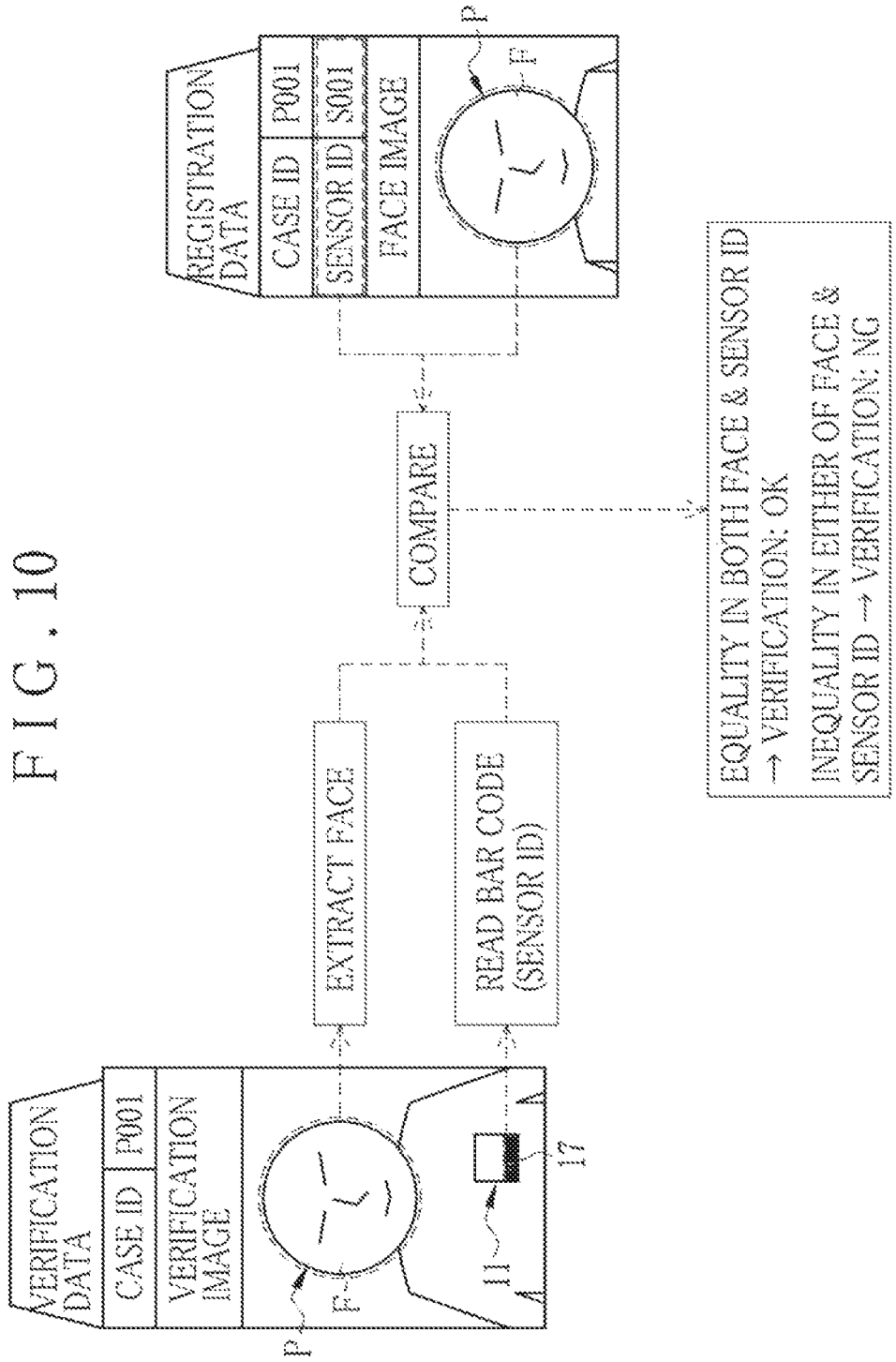
FIG. 10 is a flow chart illustrating steps of verification.

In FIG. 10, the verifier 51 processes the verification image of the verification data from the acquisition device 50 in the processing of face extraction well-known technically, and extracts a face F of the patient P. The verifier 51 also reads the bar code 17 or the sensor ID from the verification image by well-known bar code reading processing of the verification image.

The verifier 51 performs comparison between the face F extracted from the verification image and the face F in the reference image in the reference data from the data control unit 56. The verifier 51 also performs comparison between the sensor ID read from the verification image and the sensor ID in the reference data.

Assuming that the face F extracted from the verification image (identification image) coincides with the face F in the registered image of the registration data, and assuming that the sensor ID read from the verification image coincides with the sensor ID in the registration data, then the verifier 51 outputs a verification result of acceptability (OK) by determining correctness in the combination between the physiological sensor 11 and the patient P (examinee). Assuming that the face F extracted from the verification image does not coincide with the face F in the registered image of the registration data, or assuming that the sensor ID read from the verification image does not coincide with the sensor ID in the registration data, then the verifier 51 outputs a verification result of unacceptability (NG) by determining incorrectness in the combination between the physiological sensor 11 and the patient P.

Figure 11:
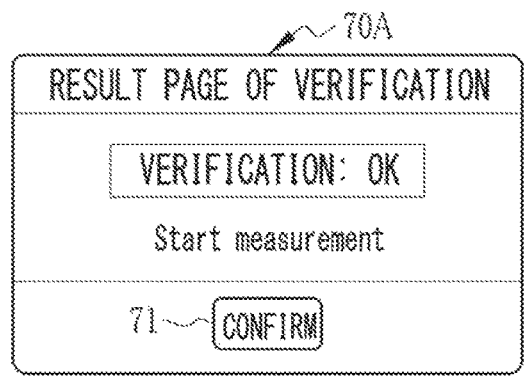
FIG. 11 is a screen view illustrating a result page of the verification.
Figure 12:
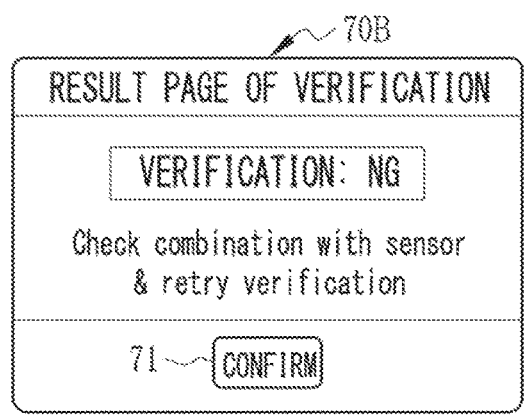
FIG. 12 is a screen view illustrating a result page in which a result of the verification is unacceptability.

In FIGS. 11 and 12, the output device 55 outputs the result pages 70A and 70B to the client terminal device 12 to indicate result information of the verification in the verifier 51. A confirm button 71 is disposed in each of the result pages 70A and 70B. In case the confirm button 71 is pressed, the result pages 70A and 70B are hidden in the display.

The result page 70A in FIG. 11 is in the form of the verification result of acceptability (OK), and indicates the information of the verification result of acceptability and a message of encouraging a start of measuring the physiological sensor 11. The result page 70B in FIG. 12 is in the form of the verification result of unacceptability (NG), and indicates the information of the verification result of unacceptability and a message of encouraging a retry for verification after checking the combination of the physiological sensor 11 and the like. It is possible audibly to output the verification result or the message through the audio speaker 19.

Figure 13:
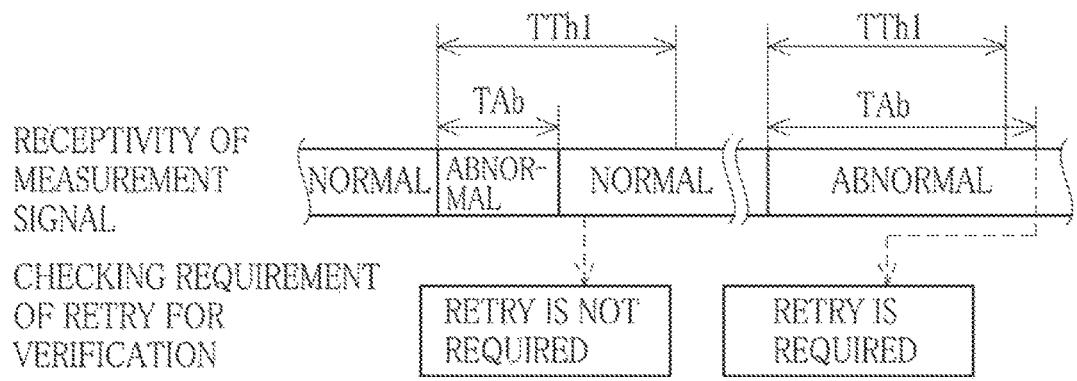
FIG. 13 is a timing chart illustrating checking requirement of a retry for the verification according to a time duration of abnormality.

In FIG. 13, the checker 54 checks whether the retry for verification in the verifier 51 is required according to the time duration TAb of continuing a state of detecting the abnormality in the receptivity of the measurement signal. Assuming that the time duration TAb is equal to or less than the reference time TTh1, then the checker 54 determines non-requirement of the retry for verification in the verifier 51, because the receptivity of the measurement signal recovers to normality within the reference time TTh1 after detecting the abnormality of the receptivity (TAb≤TTh1). Assuming that the time duration TAb becomes more than the reference time TTh1, then the checker 54 determines requirement of the retry for verification in the verifier 51 (TAb>TTh1). Note that an example of the reference time TTh1 is in a range from several seconds to several tens of seconds as a value suitable for reliably detecting non-requirement of the retry for verification in a situation without requiring the retry for verification, for example, instantaneous interruption.

In FIG. 14, the first message page 75 contains a message and a transition button 76. The message is a text of requirement of a retry for verification and guide for the patient P to the verification page 60. The transition button 76 is operable for transition of the screen to the verification page 60. Also, the message voice 77 of a message of requirement of a retry for verification is emitted.

Figure 15:
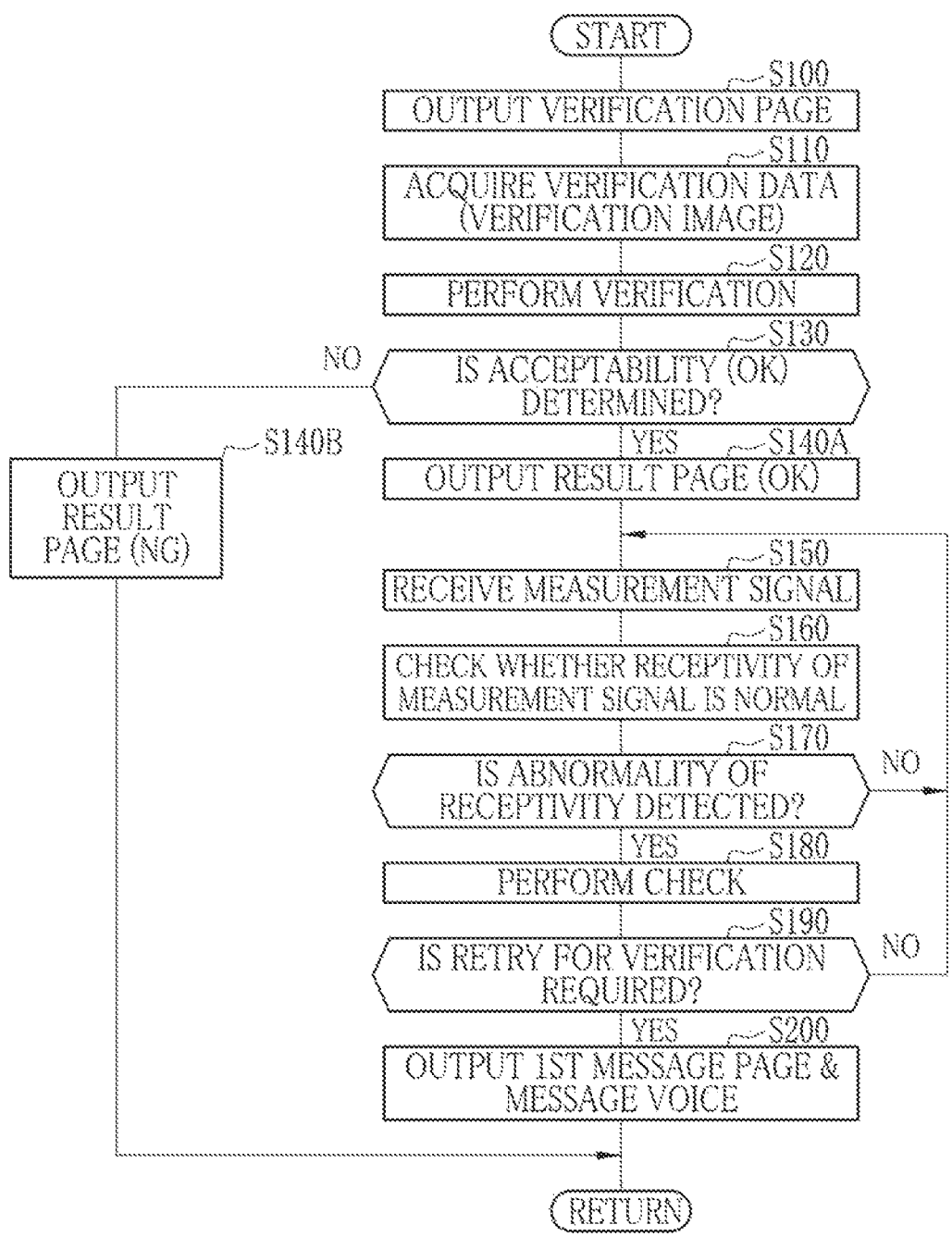
FIG. 15 is a flow chart illustrating control of the physiological sensor controller.

The operation of the above construction is described by referring to FIG. 15. The patient P at the home 14 positions the physiological sensor 11 from the medical facility 15 correctly on his or her body. The client terminal device 12 is manually operated to run the web browser, to perform access to the physiological sensor controller 13.

In case the client terminal device 12 performs access to the physiological sensor controller 13, the physiological sensor controller 13 causes the output device 55 (notification processor) to output the verification page 60 to the client terminal device 12 in a step S100. The touchscreen device 18 in the client terminal device 12 displays the verification page 60.

The patient P input his or her case ID to the input box 61 in the verification page 60. An angle of view of the camera 20 is adjusted manually for containing the bar code 17 and the face F in a portion of a frame by visually utilizing the live view frame 62 to optimize the angle of view for a verification image. He or she presses the start button 63 to form the verification image. Then the OK button 64 is pressed. The verification data including the case ID and the verification image is sent by the client terminal device 12 to the physiological sensor controller 13.

The verification data is acquired by the acquisition device 50 in a step S110 or acquisition step. The acquisition device 50 inputs the verification data to the verifier 51 and the data control unit 56.

The data control unit 56 acquires registration data from the data management server 22, the registration data having the case ID coinciding with that of the verification data from the acquisition device 50. The registration data is transferred from the data control unit 56 to the verifier 51.

The verifier 51 checks correctness in the combination between the patient P and the physiological sensor 11 according to the verification image and the registration data in a step S120 or verification step. To this end, the face F of the patient P is extracted from the verification image, and the bar code 17 of the sensor ID is read. The face F extracted from the verification image is compared with the face F in the registered image of the registration data for checking. The sensor ID read from the verification image is compared with the sensor ID in the registration data for checking.

Assuming that the face F extracted from the verification image coincides with the face F in the registered image in the registration data, and assuming that the sensor ID read from the verification image coincides with the sensor ID in the registration data, then the verifier 51 inputs result information of acceptability (OK) of the verification to the output device 55 (yes in a step S130). Assuming that the face F extracted from the verification image does not coincide with the face F in the registered image in the registration data, or assuming that the sensor ID read from the verification image does not coincide with the sensor ID in the registration data, then the verifier 51 inputs result information of unacceptability (NG) of the verification to the output device 55 (no in the step S130).

Assuming that the result information of the verification is acceptability (OK) according to the output of the verifier 51, the output device 55 outputs the result page 70A to the client terminal device 12 in a step S140A. Assuming that the result information of the verification is unacceptability (NG) according to the output of the verifier 51, the output device 55 outputs the result page 70B to the client terminal device 12 in a step S140B. In the client terminal device 12, either one of the result pages 70A and 70B is displayed on the touchscreen device 18.

In case the result page 70A is displayed, the patient P turns on the power supply for the physiological sensor 11 and causes the battery to power the physiological sensor 11, to start measuring the physiological information. In case the result page 70B is displayed, the patient P manually checks the combination with the physiological sensor 11 and the like, and performs access to the physiological sensor controller 13 again to retry verification by use of the verification page 60.

In case the measurement of the physiological information is started, the physiological sensor 11 wirelessly transmits a measurement signal to the physiological sensor controller 13 at a predetermined period. The receiver 52 receives the measurement signal in a step S150 or receiving step. The receiver 52 sets the measurement signal to the detector 53 and the data control unit 56.

The detector 53 checks whether receptivity of the measurement signal is normal or not in a step S160 or detecting step. Assuming that the measurement signal discontinues for a predetermined time, or assuming that a signal level of the measurement signal continues not to be within a predetermined range for a predetermined time, then the detector 53 detects abnormality of the receptivity of the measurement signal (yes in a step S170). The detector 53 sets the result of the detection to the checker 54.

The checker 54 checks whether the retry for verification in the verifier 51 is required by comparison between the reference time TTh1 and the time duration TAb of a condition of detecting abnormality in the receptivity of the measurement signal, in a step S180 or detecting step. Assuming that the time duration TAb is shorter than the reference time TTh1 (TAb≤TTh1), then it is judged that the retry for verification in the verifier 51 is unnecessary (no in a step S190). Assuming that the time duration TAb is longer than the reference time TTh1 (TAb>TTh1), then it is judged that the retry for verification in the verifier 51 is necessary (yes in the step S190).

Thus, suitable predetermination of the reference time TTh1 makes it possible to determine non-requirement of the retry for verification reliably for a relevant situation, such as instantaneous interruption, because the requirement of the retry for verification is determined by the verifier 51 according to the time duration TAb of a state of detecting abnormality in the receptivity of the measurement signal.

Assuming that the checker 54 determines the requirement of the retry for verification (yes in the step S190), the output device 55 outputs the first message page 75 and the message voice 77 to the client terminal device 12 in a step S200 as an output step. In the client terminal device 12, the touchscreen device 18 displays the first message page 75. The audio speaker 19 emits the message voice 77.

The patient P upon notification of the first message page 75 and the message voice 77 presses the transition button 76 to display the verification page 60 on the touchscreen device 18, and performs retry for verification by use of the verification page 60. Those steps of a sequence are continued until the end of the measurement of the physiological information.

The first message page 75 and the message voice 77 are output only upon detecting abnormality of the receptivity of the measurement signal in the detector 53 and also judging requirement of a retry for verification in the checker 54. The first message page 75 and the message voice 77 are not output in the event of non-requirement of a retry for verification. Consequently, the retry for verification can be performed by the patient P only in case the retry for verification is required actually, namely, in case the first message page 75 and the message voice 77 are output. It is possible to remove useless manipulation of the patient P for an unnecessary retry for verification.

[Second Embodiment]

In the first embodiment, the requirement of retry for verification is checked according to the time duration TAb of the state of detecting abnormality in the receptivity of the measurement signal. In contrast, the requirement of retry for verification is checked in FIGS. 16-18 according to a result of comparison between the measurement signal before detecting the abnormality in the receptivity and a measurement signal after recovery of the receptivity to the normality.

Figure 16:
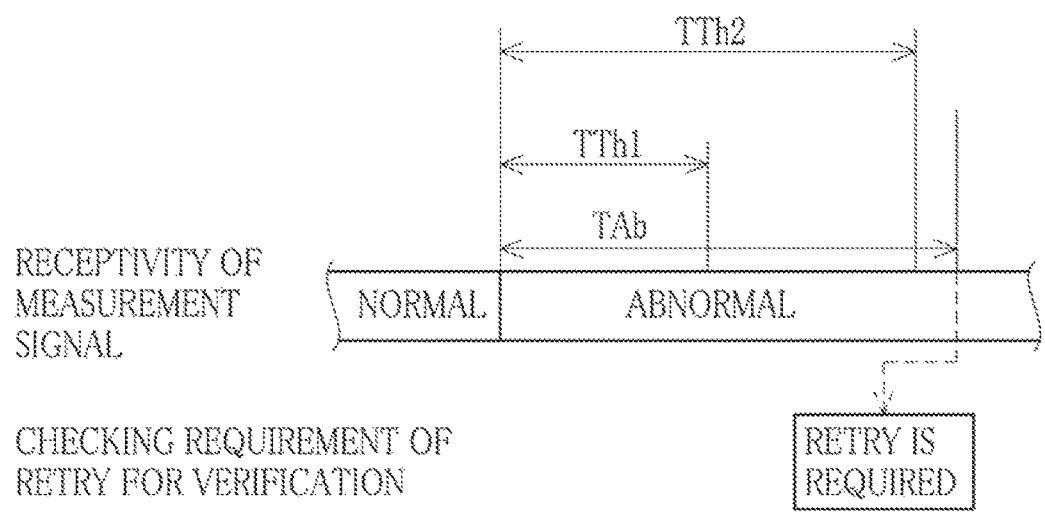
FIG. 16 is a timing chart illustrating a second preferred embodiment in which requirement of a retry for verification is checked.
Figure 17:
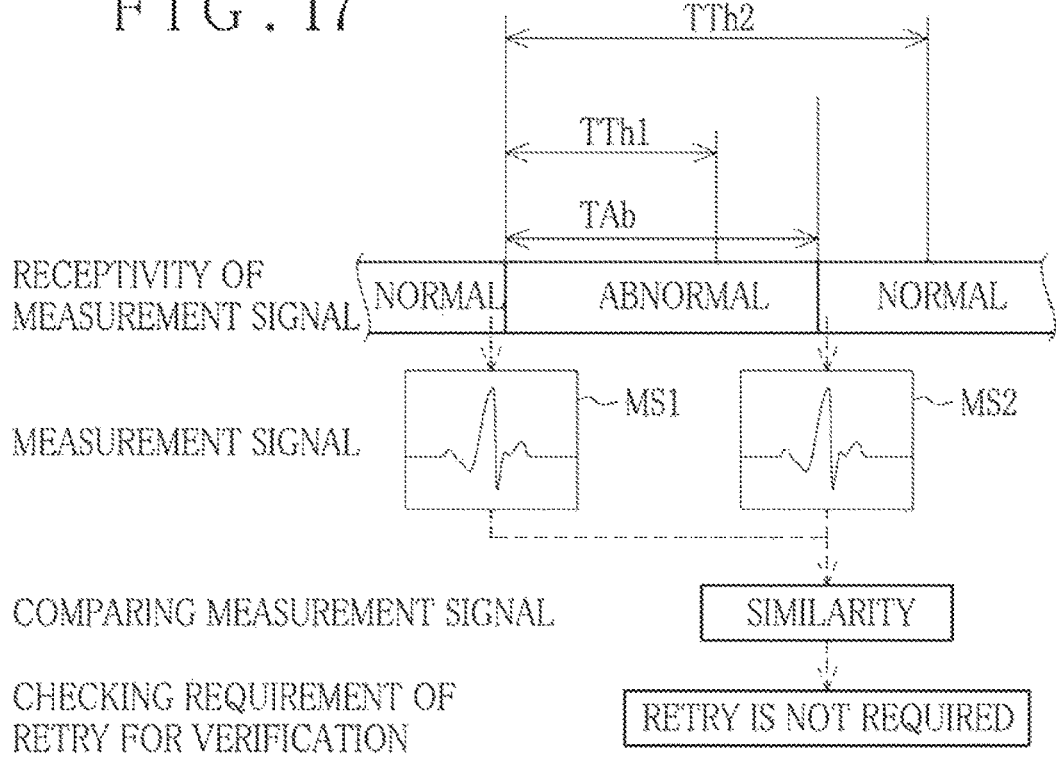
FIG. 17 is a timing chart illustrating occurrence of similarity between measurement signals.
Figure 18:
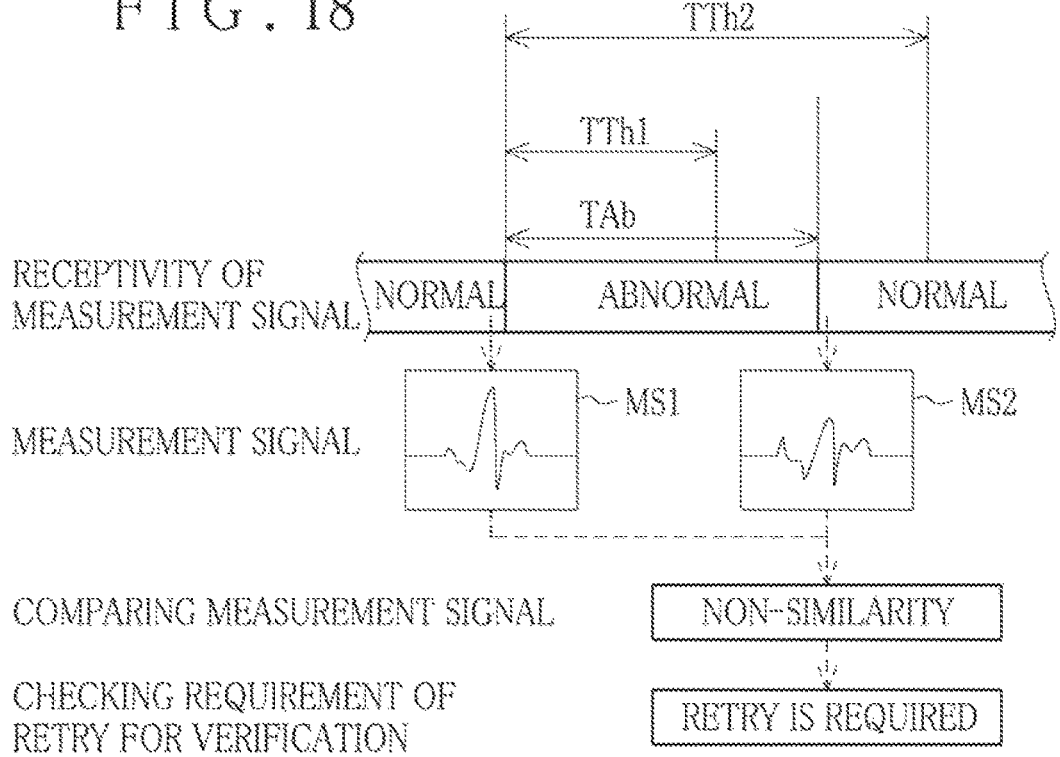
FIG. 18 is a timing chart illustrating occurrence of non-similarity between the measurement signals.

In FIGS. 16-18, reference time TTh2 is preset in addition to the reference time TTh1 of the first embodiment with a larger length than the reference time TTh1. For example, the reference time TTh2 is two times as long as the reference time TTh1. The receiver 52 inputs a measurement signal to the checker 54, which has a memory for temporarily storing the measurement signal of plural times of the sampling.

At first, assuming that the time duration TAb of the state of detecting abnormality in the receptivity of the measurement signal becomes longer than the reference time TTh1 and also longer than the reference time TTh2 (TAb>TTh1 and TAb>TTh2), then the checker 54 in FIG. 16 determines requirement of a retry for verification.

Assuming that the time duration TAb is longer than the reference time TTh1 but equal to or shorter than the reference time TTh2 as illustrated in FIGS. 17 and 18, namely, assuming that the receptivity of the measurement signal is recovered to normality within the reference time TTh2 after detecting the abnormality of the receptivity of the measurement signal (TTh1<TAb≤TTh2), then the checker 54 compares the stored measurement signal MS1 before detecting the abnormality of the receptivity and the measurement signal MS2 from the receiver 52 after the recovery to the normality of the receptivity.

In case the measurement signals MS1 and MS2 are similar to one another in FIG. 17 (in case the result of the comparison between the measurement signals MS1 and MS2 is similarity), the checker 54 determines non-requirement of the retry for verification. However, in case the measurement signals MS1 and MS2 are not similar to one another in FIG. 18 (in case the result of the comparison between the measurement signals MS1 and MS2 is non-similarity), the checker 54 determines requirement of the retry for verification. Note that succeeding steps of the operation are the same as those of the first embodiment.

Assuming that the measurement signals MS1 and MS2 are not similar to one another, it is likely with high possibility that the patient P before detecting abnormality of the receptivity is different from the patient P after recovery to the normality of the receptivity, due to specificity in the measurement signal between plural patients. It is judged that the retry for verification is required in the case of non-similarity between the measurement signals MS1 and MS2, so as to output a message of encouraging the retry for verification to the patient P. In contrast, assuming that the measurement signals MS1 and MS2 are similar to one another, it is likely with high possibility that the patient P before detecting abnormality of the receptivity is identical with the patient P after the recovery to the normality of the receptivity. Thus, it is judged that the retry for verification is not required.

Thus, the requirement of retry for verification is checked according to a result of comparison between the measurement signal MS1 before detecting abnormality in the receptivity and the measurement signal MS2 after recovery of the receptivity to the normality. It is possible to determine non-requirement of the retry for verification assuming that no retry for verification is required, for example, in case the patient P removes the physiological sensor 11 temporarily and repositions the physiological sensor 11 very immediately for the purpose of correct positioning. It is possible to reduce waste operation with the patient P in relation to unwanted retry for verification.

In contrast, assuming that the time duration TAb is longer than the reference time TTh2, for example, assuming that the patient removes the physiological sensor 11 for a relatively long time due to taking a bath or the like, then it is judged that a retry for verification is necessary without comparing the measurement signals MS1 and MS2 in FIG. 16. Furthermore, assuming that non-similarity is found between the measurement signals MS1 and MS2 in spite of the time duration TAb equal to or shorter than the reference time TTh2, then it is judged that a retry for verification is required, because impersonation of a stranger in place of the patient P is suspected. In conclusion, the retry for verification can be performed in case the retry for verification is required actually.

In FIGS. 16-18, the example of the measurement signal is the ECG waveform signal output by the an ECG sensor as the physiological sensor 11. Checking similarity between the measurement signals MS1 and MS2 is enabled by comparing shapes of ECG waveforms, for example, locations and/or potentials of peaks P, Q, R, S and T of the ECG waveform as well-known data in the medical field. Also, the physiological sensor 11 can be a body temperature sensor. The measurement signal can be a signal of the body temperature of the patient P. Assuming that the body temperature expressed by the measurement signal MS2 is within a range of the body temperature expressed by the measurement signal MS1±α, then similarity between the measurement signals MS1 and MS2 is determined. Assuming that the body temperature expressed by the measurement signal MS2 is not within the range of the body temperature expressed by the measurement signal MS1±α, then non-similarity between the measurement signals MS1 and MS2 is determined.

[Third Embodiment]

In general, a correct sensor position where the physiological sensor 11 should be mounted on the patient body is predetermined. The sensor position may differ between patients P for the reason of differences in the size of the patient body. Also, plural sensor positions should be predetermined in combination with plural diseases or health problems of the patients P even in the use of the same physiological sensor 11. Should the physiological sensor 11 be positioned in an incorrect position, reliability of physiological information from the physiological sensor 11 may be lower medically. Also, the detector 53 may detect abnormality of the receptivity of the measurement signal due to the incorrectness of the sensor position, so that the retry for verification may be required.

The sensor position of the physiological sensor 11 can be recognized in the verification image. In FIGS. 19-26, the sensor position of the physiological sensor 11 is detected by use of the verification image, and a message of incorrectness in the sensor position is output assuming that the sensor position is incorrect.

Figure 19:
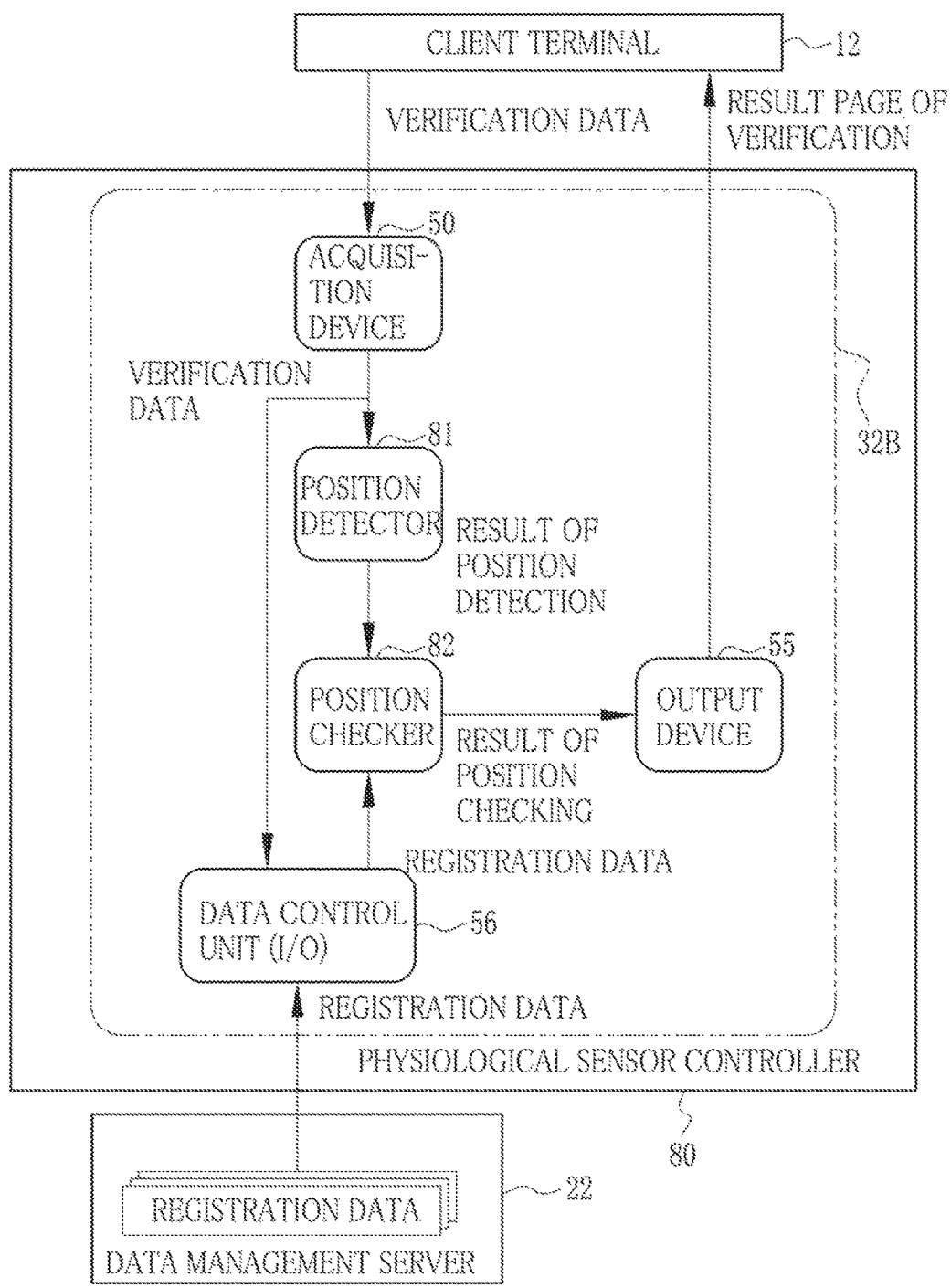
FIG. 19 is a block diagram schematically illustrating circuit devices in a third preferred physiological sensor controller.

In FIG. 19, a physiological sensor controller 80 (physiological monitoring apparatus) is illustrated, in which a position detector 81 and a position checker 82 are established in the CPU 32B in addition to the circuit devices 50-56 of the first embodiment. The circuit devices 51-54 are not shown in the drawing of the embodiment.

The position detector 81 receives verification data from the acquisition device 50, and detects the sensor position of the physiological sensor 11 according to the verification image in the verification data. The position detector 81 sets a result of the position detection to the position checker 82. The position checker 82 checks whether the sensor position of the physiological sensor 11 is correct or not according to the result information of the position detection from the position detector 81 and the registration data from the data control unit 56. The position checker 82 inputs result information of position checking to the output device 55.

Assuming that the result information of position checking from the position checker 82 is that the sensor position detected by the position detector 81 is incorrect, then the output device 55 outputs a result page 85C (in FIG. 24) or a result page 85D (in FIG. 25) for a verification result to the client terminal device 12, as a form of informing the incorrectness in the sensor position of the physiological sensor 11.

Figure 20:
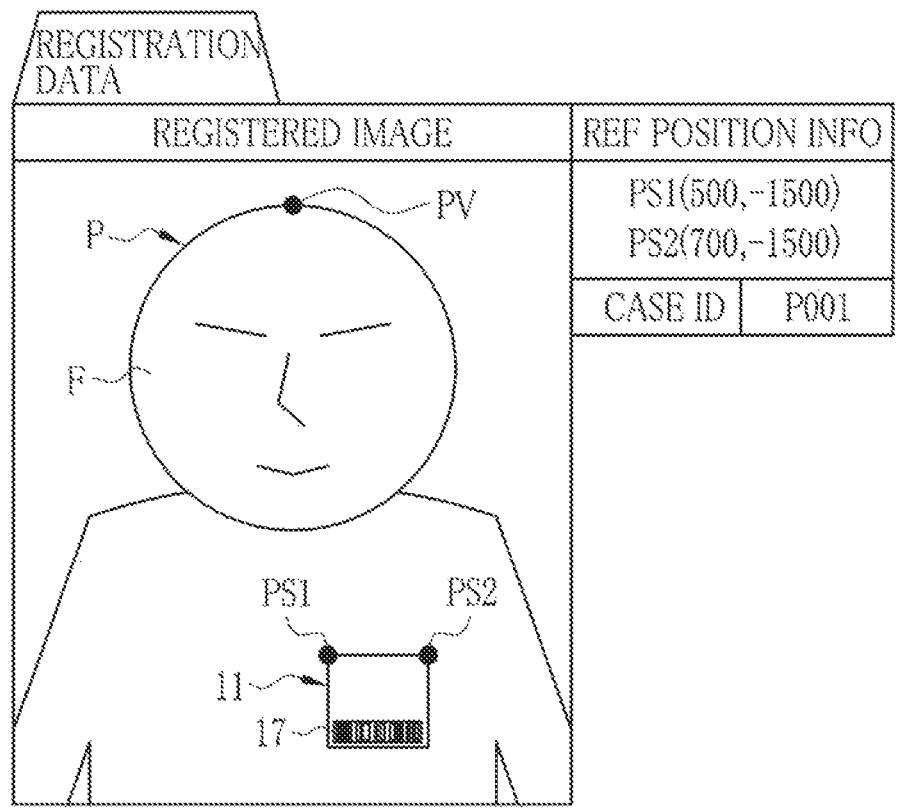
FIG. 20 is a data chart illustrating registration data.

In FIG. 20 of the present embodiment, reference position information is registered in the registration data with registered image, and denotes a correct sensor position of the physiological sensor 11. The registered image is initially taken while the physiological sensor 11 is positioned in the correct sensor position. The reference position information is extracted by use of a well-known technique of image recognition of the registered image. An example of the reference position information is coordinates of two points in the physiological sensor 11 within the registered image as information with reference to the origin predetermined at a particular body part of the body of the patient P in the registered image. In FIG. 20, the particular body part is a head top PV. The two points in the physiological sensor 11 are upper points PS1 and PS2.

Figure 21:
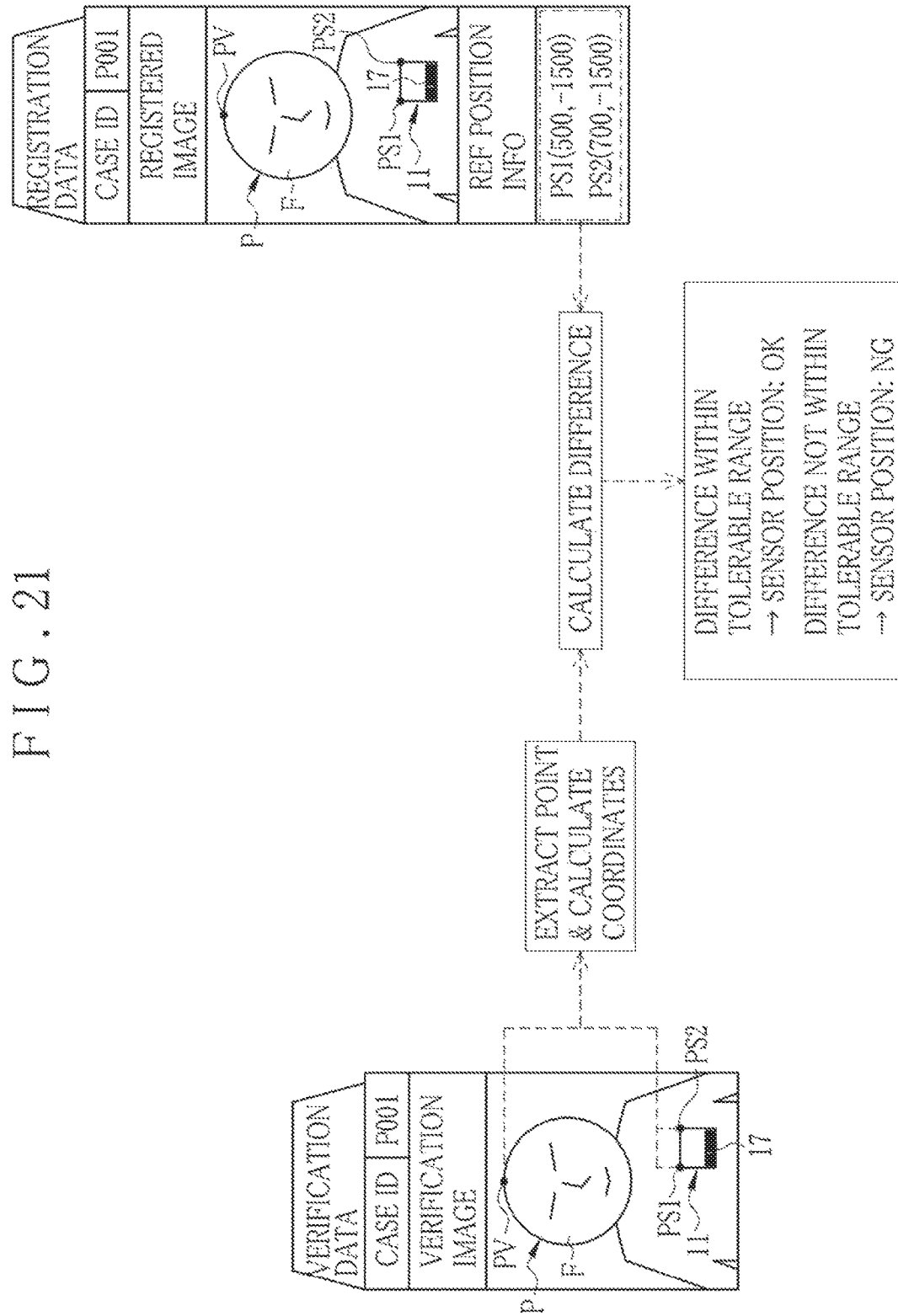
FIG. 21 is a flow chart illustrating position detection and position checking.

In FIG. 21, the position detector 81 processes the verification image (identification image) in the verification data (identification data) from the acquisition device 50 in the image recognition as well-known processing, in the same manner as extraction of the reference position information from the registered image, so as to extract the head top PV and upper points PS1 and PS2 of the physiological sensor 11. Then the position detector 81 determines coordinates of the upper points PS1 and PS2 with reference to the origin at the head top PV. The position detector 81 outputs the coordinates of the upper points PS1 and PS2 to the position checker 82 as result information of the detected position. Note that the position detector 81 performs pretreatment of the verification image before the extraction of the points, the pretreatment being processing of enlargement, reduction or rotation of the verification image, for adjustment of the size and direction in the same manner as the patient P and the physiological sensor 11 of image portions in the registered image.

The position checker 82 calculates a difference between coordinates of the points PS1 and PS2 from the position detector 81 and coordinates of the points PS1 and PS2 of the reference position information of the sensor position in the registration data. Assuming that the difference is within a tolerable range, then the position checker 82 outputs result information of acceptability (OK) of the sensor position. Assuming that the difference is not within the tolerable range, then the position checker 82 outputs result information of unacceptability (NG) of the sensor position.

Figure 22:
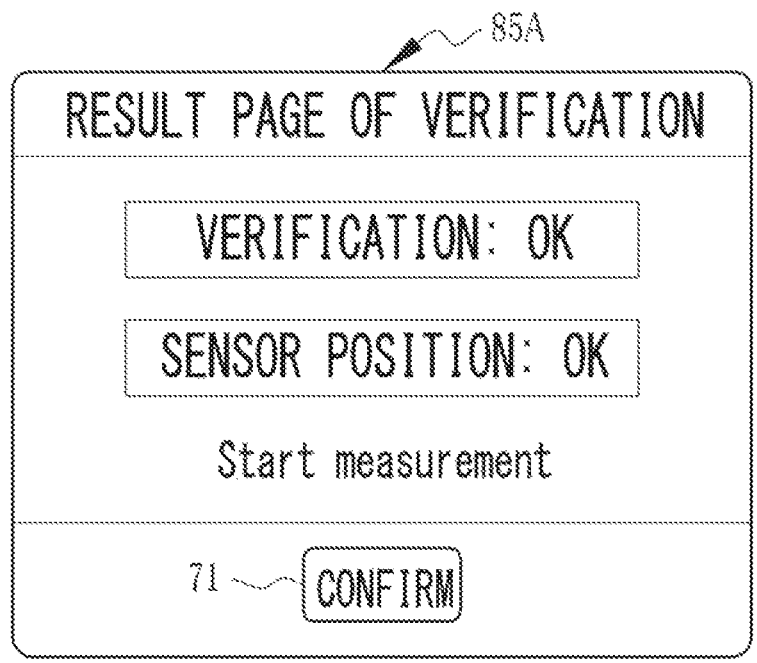
FIG. 22 is a screen view illustrating a result page.
Figure 23:
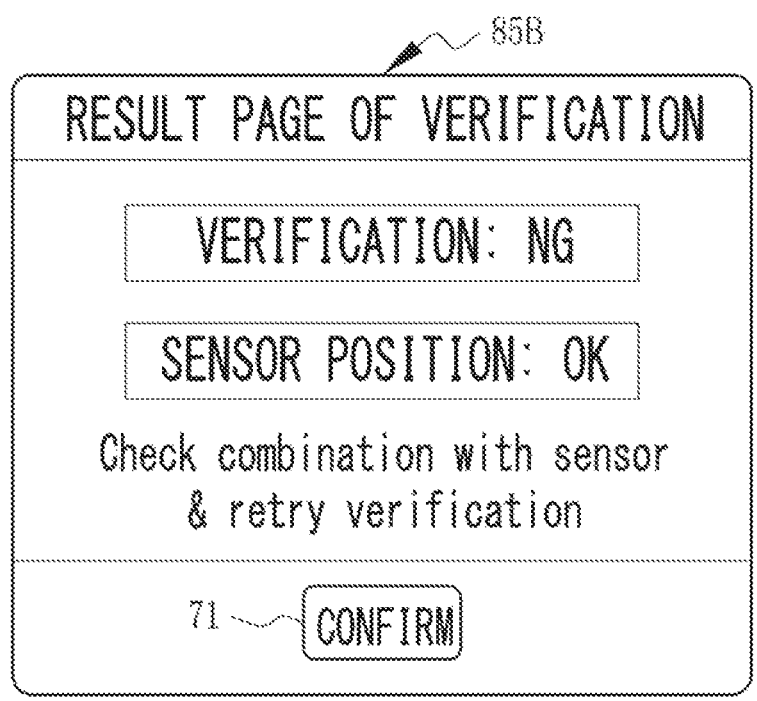
FIG. 23 is a screen view illustrating a result page in which a result of the verification is unacceptability.

For the result of correctness of the sensor position in the position checking, the output device 55 outputs a result page 85A of FIG. 22 or a result page 85B of FIG. 23 to the client terminal device 12. In the result page 85A, both results of the verification and the position checking are acceptability (OK). Acceptability (correctness) of the sensor position is indicated in addition to the information of the result page 70A of FIG. 11. In the result page 85B, the result of the verification is unacceptability (NG) in contrast with acceptability in the position checking. Acceptability (correctness) of the sensor position is indicated in addition to the information of the result page 70B of FIG. 12.

Figure 24:
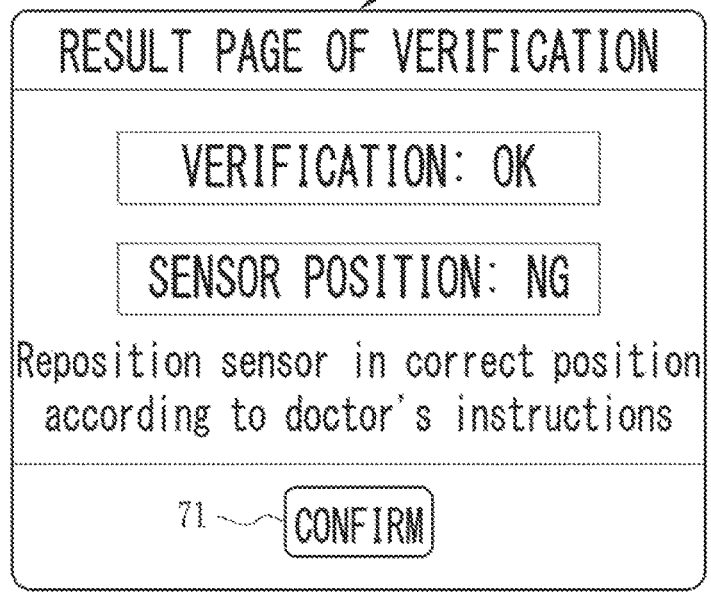
FIG. 24 is a screen view illustrating a result page in which a result of the position checking is unacceptability.
Figure 25:
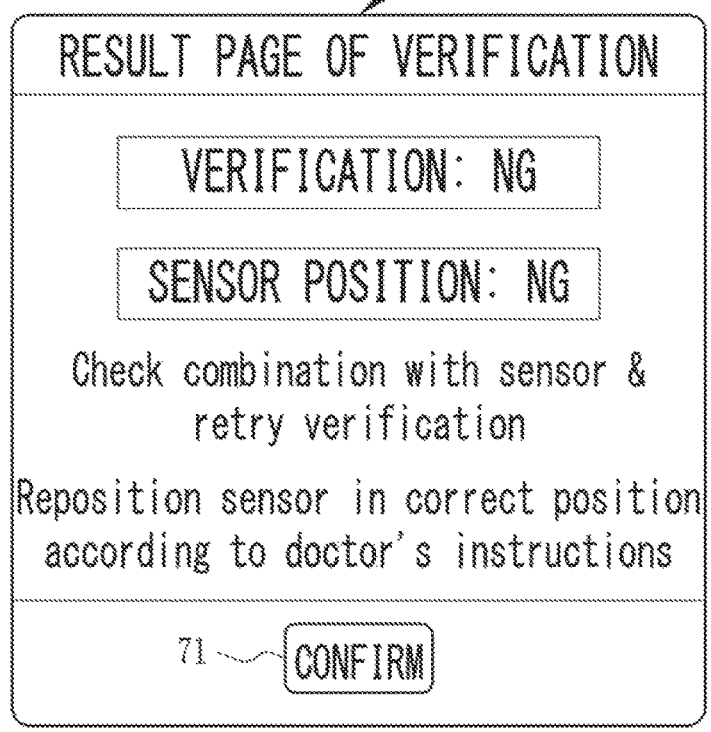
FIG. 25 is a screen view illustrating a result page in which results of the verification and the position checking are unacceptability.

Assuming that the result information of unacceptability (incorrectness) of the sensor position is obtained, the output device 55 outputs the result page 85C of FIG. 24 or the result page 85D of FIG. 25 to the client terminal device 12. In the result page 85C, the result of the verification is acceptability (OK) but the result of the position checking is incorrectness (NG). The result page 85C indicates information of incorrectness (NG) of the sensor position and a message for encouraging positioning of the physiological sensor 11 in a corrected sensor position, in addition to information in the result page 70A in FIG. 11. In the result page 85D, the results of the verification and the position checking are unacceptability (NG). The result page 85D indicates information of unacceptability (NG) of the sensor position and a message for encouraging positioning of the physiological sensor 11 in a corrected sensor position, in addition to information in the result page 70B in FIG. 12.

In short, the sensor position of the physiological sensor 11 is detected according to the verification image. Assuming that the detected sensor position is incorrect, a message for informing the incorrectness of the sensor position is output. It is possible to prevent measurement of the physiological information while the sensor position is incorrect, to obtain high reliability of the physiological information. Also, the sensor position can be detected together with checking correctness in a combination between the physiological sensor 11 and the patient P (examinee).

Also, it is possible to detect the sensor position with high precision, as the sensor position is detected according to a relative position in relation to a particular body part of the body of the patient P in the verification image. Note that examples of the particular body part of the patient P can be a nipple of breast, a tip of a finger, a vein in an arm, or the like.

Instead of registering the reference position information, it is also possible to store the reference position information in (a storage medium in) the physiological sensor 11 and retrieve the same from the physiological sensor 11. Furthermore, a plurality of information items of the reference position information can be stored for plural symptoms in view of plural sensor positions which are predetermined for the plural symptoms of the patients P with local differences. Information of the symptom of each of the patients P can be read out from an EMR (electronic medical record) managed in the medical facility 15, so that the reference position information can be selected according to the particular symptom of the patient P.

Figure 26:
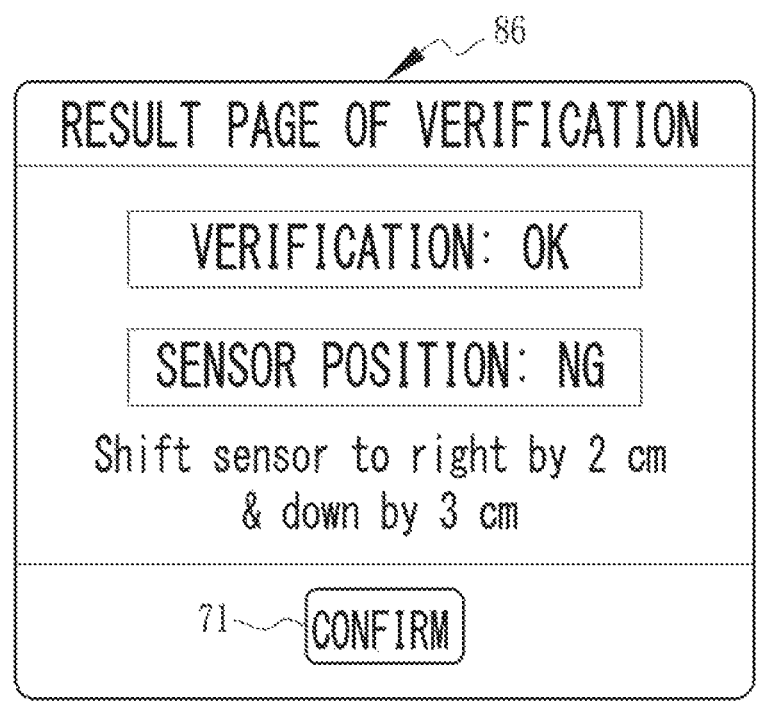
FIG. 26 is a screen view illustrating a result page with guide information for correcting the sensor position.

In FIGS. 24 and 25, the message for encouraging acceptable positioning of the physiological sensor 11 is indicated in the result pages 85C and 85D. However, a message of detailed expressions can be indicated. In FIG. 26, a result page 86 for a verification result is illustrated. A message of guide information for the patient P (examinee) to reposition the physiological sensor 11 is indicated, for example, "Shift sensor to right by 2 cm and down by 3 cm". To this end, the distance of "2 cm" and the like in the message can be obtained from the difference of the coordinates determined by the position checker 82. Thus, the patient P can reposition the physiological sensor in the correct sensor position by following the guide information, to measure the physiological information always in the correct sensor position.

Other methods of notifying a correct sensor position for setting the physiological sensor 11 can be used. For example, it is possible to display a registered image obtained by correctly positioning the physiological sensor 11 in an overlapped manner with the live view frame 62 of the verification page 60. Furthermore, a laser pointer which may be combined with the client terminal device 12 for pointing a position can be utilized for notifying the correct sensor position.

Also, the result information of the position checking can be output audibly by the audio speaker 19. Furthermore, it is possible discretely to display the results of the verification and the position checking in contrast with the combined form of the result pages 85A-85D and the result page 86.

[Fourth Embodiment]

A sensor direction of directing the physiological sensor 11 is important diagnostically in addition to the sensor position. For example, it is technically known in the field of the ECG that an ECG waveform becomes inverted assuming that the direction of positive and negative electrodes is changed by 180 degrees. In FIGS. 27-35, a preferred embodiment is illustrated, in which a sensor direction of the physiological sensor 11 is detected, and assuming that the detected sensor direction is not normal, the measurement signal is corrected in a form of a measurement signal in a state of the normal sensor direction.

Figure 27:
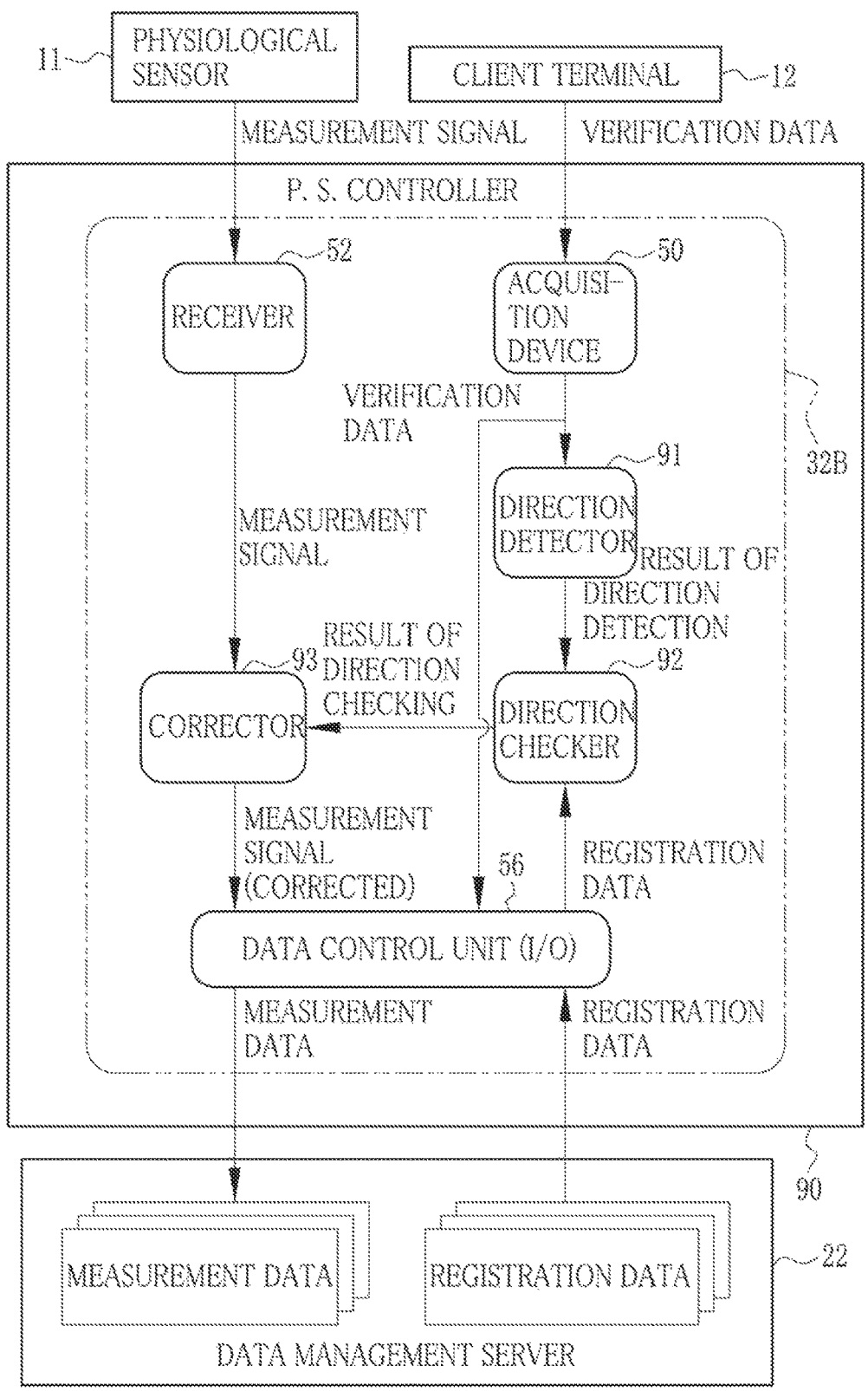
FIG. 27 is a block diagram schematically illustrating circuit devices in a fourth preferred physiological sensor controller.

In FIG. 27, running the program in the CPU 32B in a physiological sensor controller 90 (physiological monitoring apparatus) of the embodiment establishes a direction detector 91, a direction checker 92 and a corrector 93 (phase shifter) in addition to the circuit devices 50-56 of the first embodiment. The verifier 51 and the circuit devices 53-55 are not shown.

The direction detector 91 receives verification data from the acquisition device 50, and detects a sensor direction of the physiological sensor 11 according to the verification image included in the verification data. The direction detector 91 outputs result information of the direction detection to the direction checker 92. The direction checker 92 checks whether the sensor direction of the physiological sensor 11 is normal or not according to the result information of the direction detection from the direction detector 91 and the registration data from the data control unit 56. The direction checker 92 outputs result information of the direction checking to the output device 55 (not shown) and the corrector 93.

Assuming that the result information of the direction checking from the direction checker 92 is not normality in the sensor direction detected by the direction detector 91, the corrector 93 corrects the measurement signal from the receiver 52 in a form of a measurement signal in a state of normality in the sensor direction. The corrector 93 inputs the corrected measurement signal to the data control unit 56.

Figure 28:
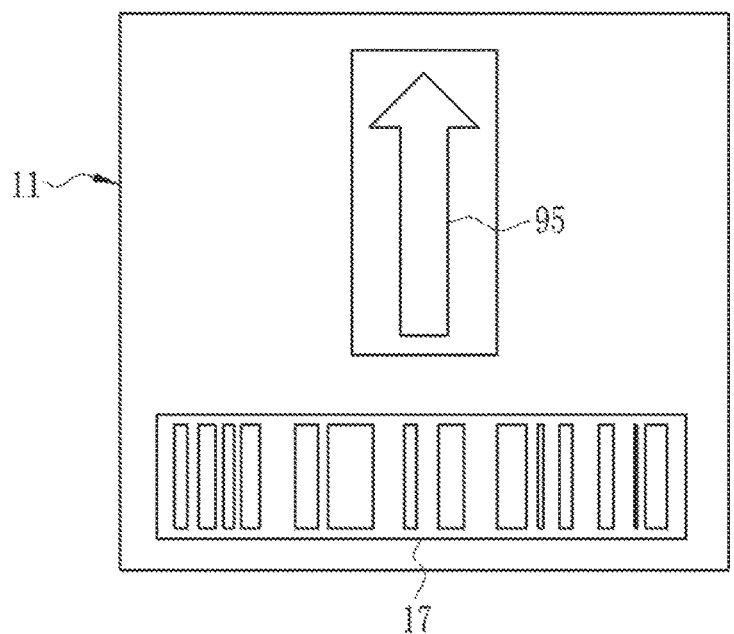
FIG. 28 is a front elevation illustrating a physiological sensor having a direction indicator.

In FIG. 28, a direction indicator 95 is disposed on the physiological sensor 11 for indicating the sensor direction. An example of the direction indicator 95 is an indicia of an arrow directed upwards with the physiological sensor 11. The physiological sensor 11 has such a property of the ECG sensor that a waveform of its measurement signal becomes inverted assuming that the direction of positive and negative electrodes is changed by 180 degrees.

Figure 29:
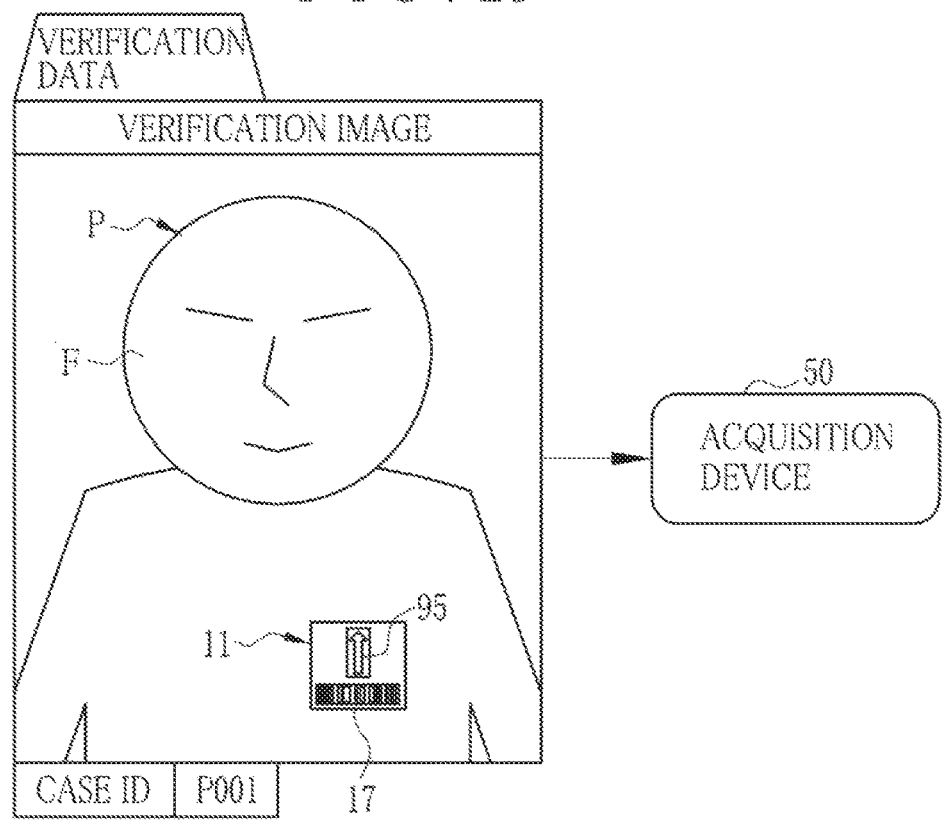
FIG. 29 is a data chart illustrating acquisition of the verification image with a portion of the direction indicator.

In FIG. 29, the acquisition device 50 of the embodiment acquires verification data including verification image containing a portion of the direction indicator 95 in addition to portions of the bar code 17 and the face F of the patient P.

Figure 30:
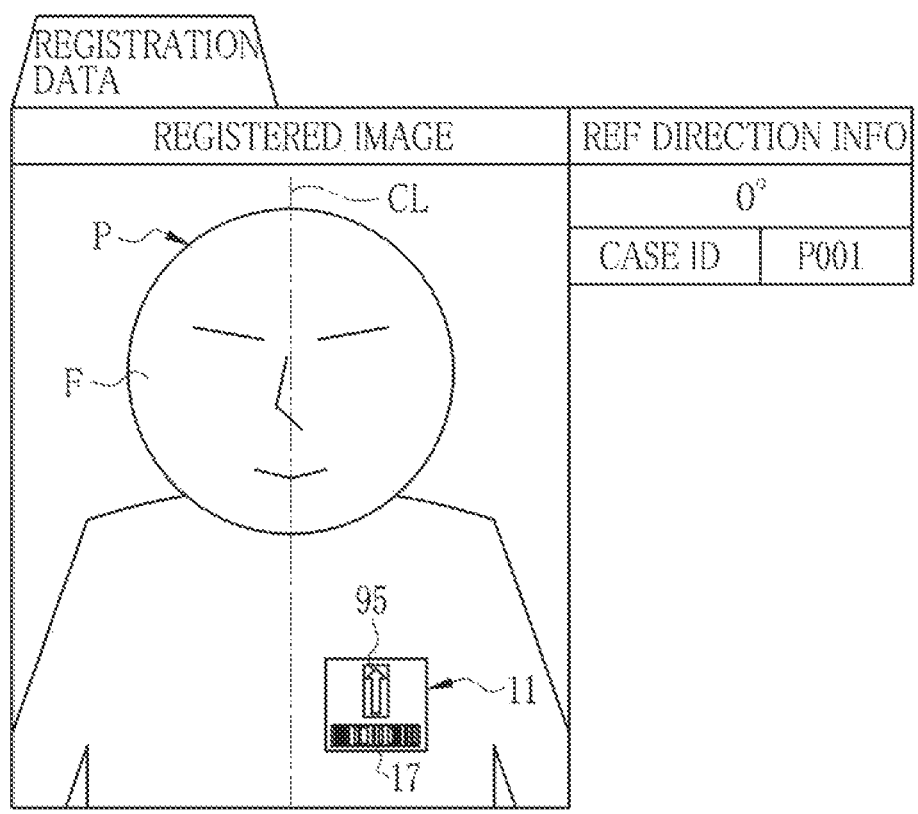
FIG. 30 is a data chart illustrating registration data in a fourth preferred embodiment.

In FIG. 30, reference direction information of a sensor direction is registered together with the registration data for expressing a normal sensor direction of the physiological sensor 11. Originally, the registered image has been formed in a state of the physiological sensor 11 directed in a normal sensor direction. The reference direction information is extracted by processing the registered image in the well-known image recognition. An example of the reference direction information is an angle defined between the direction indicator 95 and a straight line passing a specific point in a body part of the patient P in the registered image. In FIG. 30, the straight line of the specific point is the center line CL passing the head top and the center of the chest. An example of the reference direction information is zero (0) degree as an angle.

Figure 31:
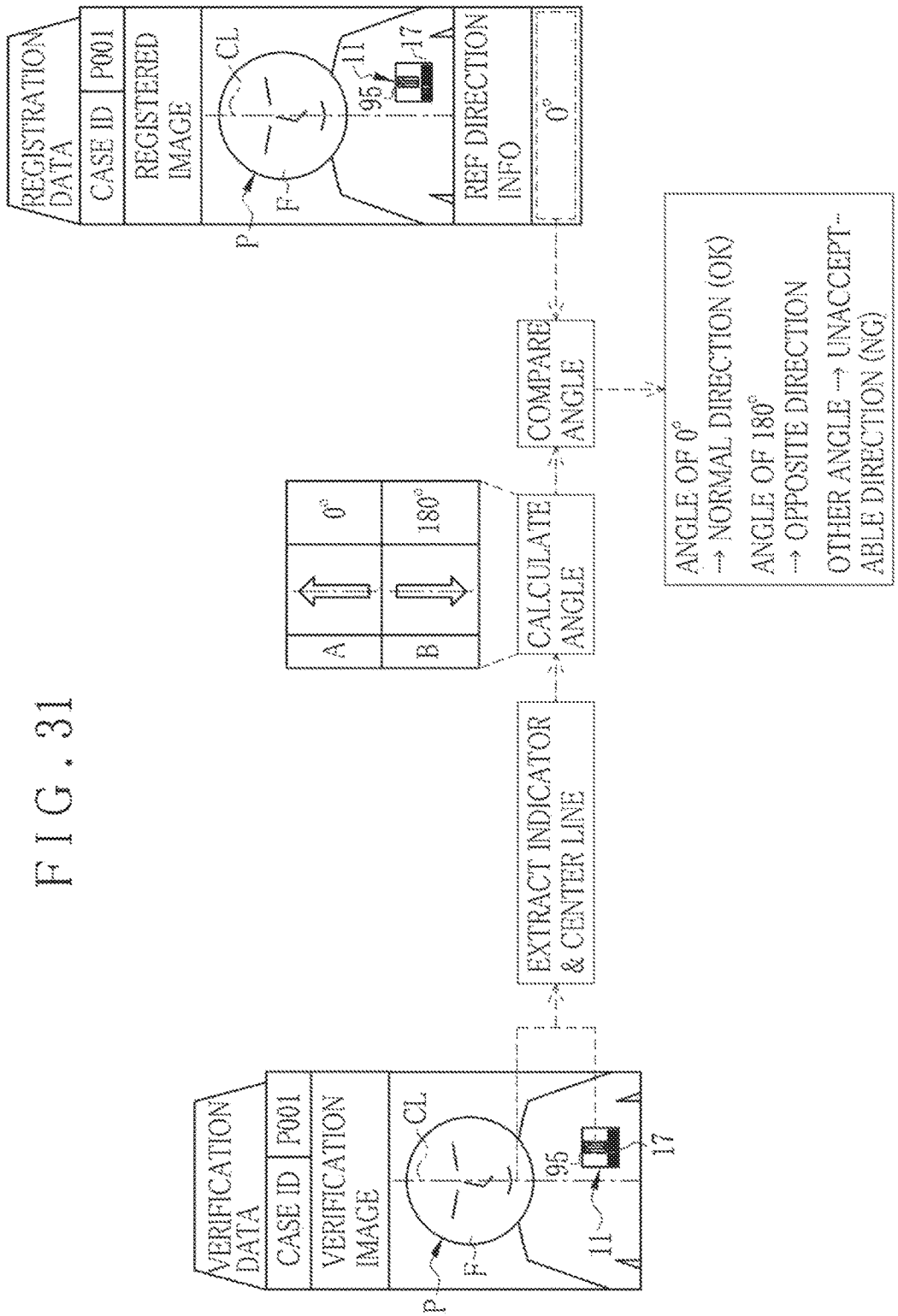
FIG. 31 is a flow chart illustrating direction detection and direction checking.

In FIG. 31, the direction detector 91 processes the verification image (identification image) in the verification data (identification data) from the acquisition device 50 in the image recognition as well-known processing, in the same manner as extraction of the reference direction information from the registered image, so as to extract the direction indicator 95 and the center line CL. Then an angle defined between the direction indicator 95 and the center line CL is obtained. For example, assuming that the direction indicator 95 and the center line CL are oriented in a pattern A (example arrangement A) in the drawing, the obtained angle is zero (0). Assuming that the direction indicator 95 and the center line CL are oriented in a pattern B, the obtained angle is 180 degrees. The direction detector 91 outputs the obtained angle to the direction checker 92 as result information of the direction detection. Note that the direction detector 91 performs pretreatment of the verification image before the extraction of the direction indicator 95 and the center line CL, the pretreatment being processing of enlargement, reduction or rotation of the verification image, for adjustment of the size and direction in the same manner as the patient P and the physiological sensor 11 of image portions in the registered image, in a manner similar to the position detector 81 of the third embodiment.

The direction checker 92 performs comparison between an angle defined between the center line CL and the direction indicator 95 by the direction detector 91 and an angle of the reference direction information according to the registration data. Assuming that the angle between the center line CL and the direction indicator 95 is 0 degree and equal to 0 degree of the angle of the reference direction information, then result information of the normality (OK) of the sensor direction is output. Assuming that the angle between the center line CL and the direction indicator 95 is 180 degrees, then result information of the opposite sensor direction (OP) is output. Assuming that the angle between the center line CL and the direction indicator 95 is different from 0 degree and 180 degrees, then result information of the unacceptability (NG) is output.

Figure 32:
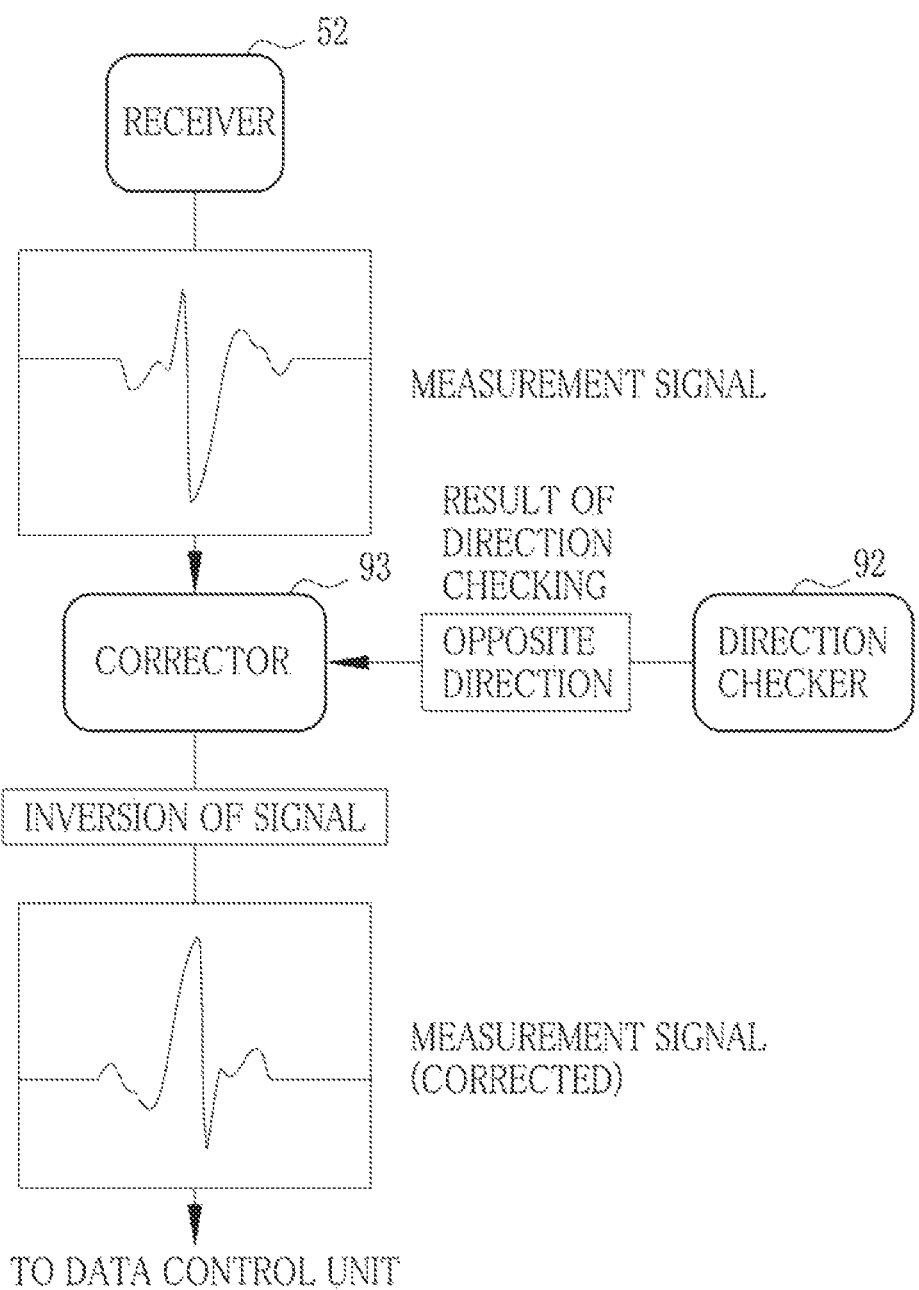
FIG. 32 is a block diagram schematically illustrating a corrector.

Assuming that the result information of the direction checking from the direction checker 92 is normality (OK) with the normal sensor direction, or unacceptability (NG) with an unacceptable sensor direction, the corrector 93 is inactive. Only assuming that the result information of the direction checking from the direction checker 92 is information of an opposite sensor direction (OP), the corrector 93 is made active. The corrector 93 in FIG. 32 processes the measurement signal from the receiver 52 in processing of signal inversion (phase inversion). Thus, the measurement signal from the receiver 52 is corrected in a form of a measurement signal in a state of the normality in the sensor direction. In FIG. 32, the measurement signal is the ECG waveform signal.

Figure 33:
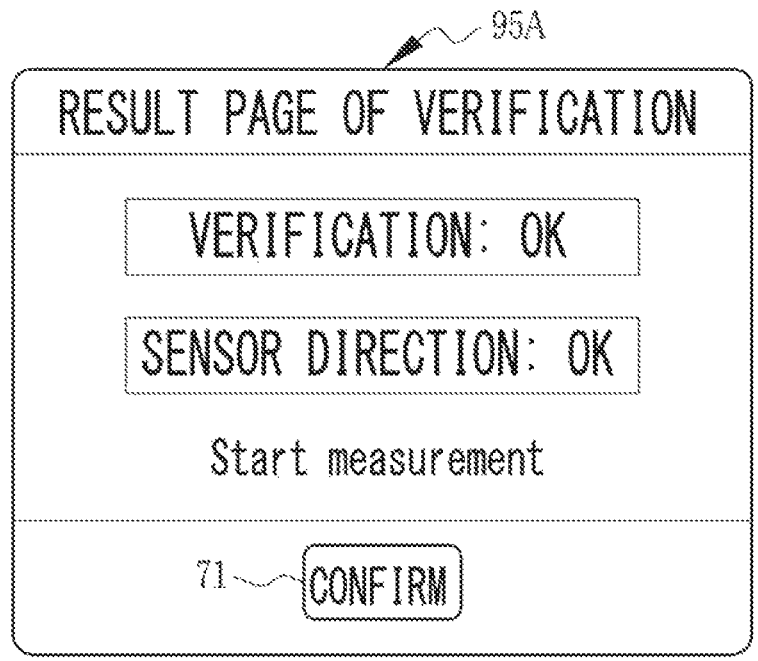
FIG. 33 is a screen view illustrating a result page.

Assuming that the result information of the direction checking from the direction checker 92 is normality (OK), then the output device 55 outputs a result page 95A for a verification result of FIG. 33 to the client terminal device 12. In the result page 95A, the result information of the verification and direction checking is acceptability (OK) and normality (OK). A message of the normality (OK) of the sensor direction is indicated in addition to the information in the result page 70A of FIG. 11.

Figure 34:
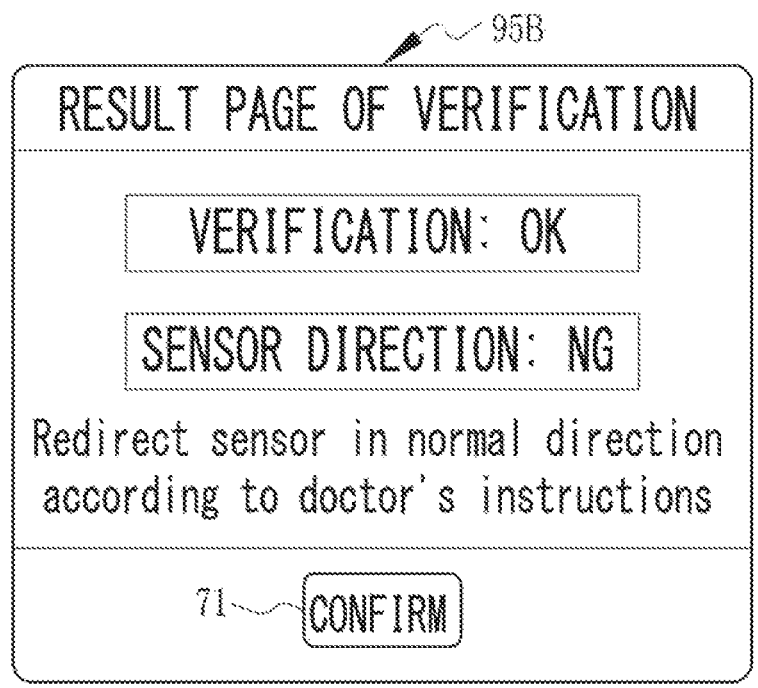
FIG. 34 is a screen view illustrating a result page in which a result of the direction checking is incorrectness.

Assuming that the result information of the direction checking from the direction checker 92 is unacceptability (NG), then the output device 55 outputs a result page 95B for a verification result of FIG. 34 to the client terminal device 12. In the result page 95B, the result information of the verification is acceptability (OK), but the result information of the direction checking is unacceptability (NG). A message of unacceptability (NG) of the sensor direction and encouragement for repositioning the physiological sensor 11 in the normal sensor direction is indicated in addition to the information in the result page 70A.

Thus, the sensor direction of the physiological sensor 11 is detected. Assuming that the detected sensor direction is not normal, the measurement signal is corrected in a form of the signal in a state of the normal sensor direction. Thus, it is possible to obtain a measurement signal correctly even assuming that the detected sensor direction is not normal.

The direction indicator 95 is positioned with the physiological sensor 11 for indicating the sensor direction. The sensor direction is detected by acquiring and reading the verification image containing the portion of the direction indicator 95. Thus, the sensor direction can be detected in combination of checking the acceptability in the combination between the physiological sensor 11 and the patient P.

Also, the result information of the direction checking can be output audibly through the audio speaker 19 in the same manner as the result information of the position checking. Furthermore, the result information of the direction checking can be displayed discretely from the verification result.

Figure 35:
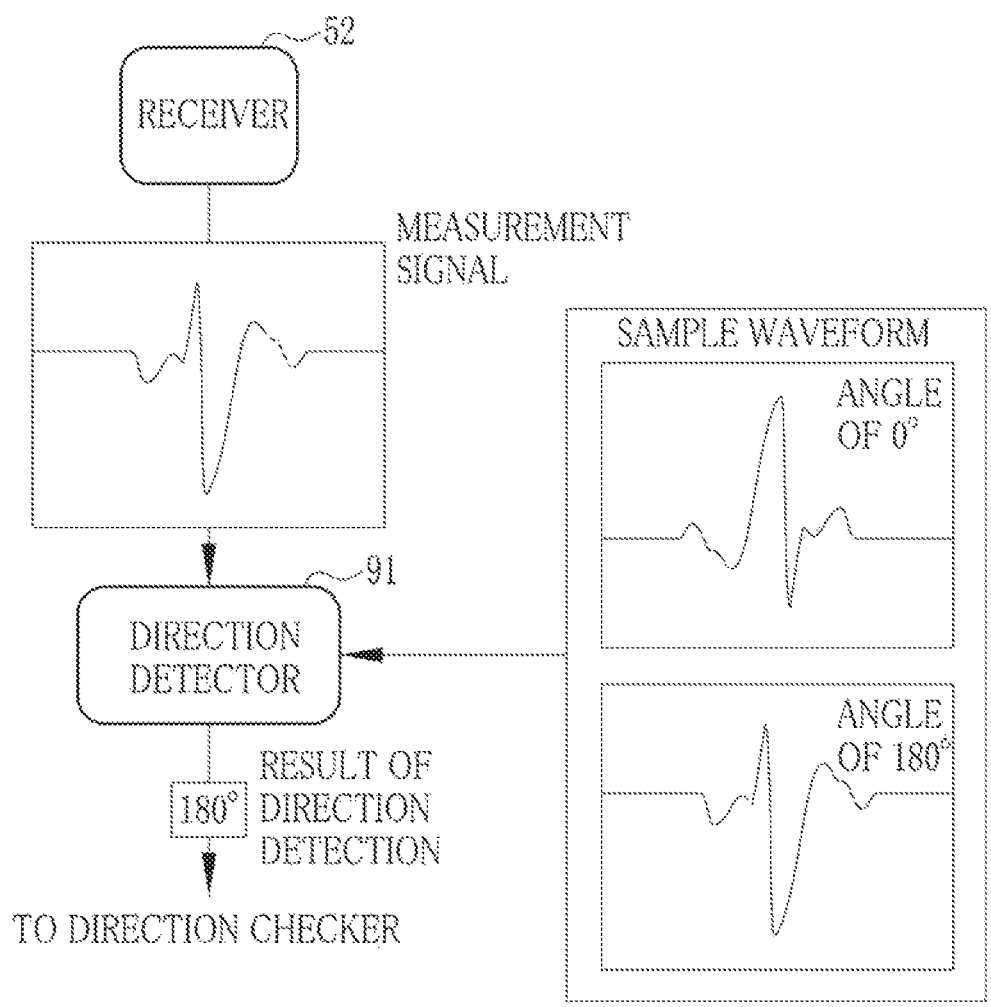
FIG. 35 is a flow chart illustrating detection of a sensor direction according to a measurement signal.

Furthermore, the sensor direction can be detected according to the measurement signal instead of using the verification image. In FIG. 35, the direction detector 91 detects the sensor direction according to a result of comparison between the waveform of the measurement signal from the receiver 52 and a sample waveform of the measurement signal for various angles defined between the direction indicator 95 and the center line CL. In FIG. 35, the waveform of the measurement signal from the receiver 52 is similar to the sample waveform of the angle of 180 degrees. The output result of detecting the direction is the angle of 180 degrees between the direction indicator 95 and the center line CL. Note that information of the sample waveform is previously stored in the storage medium 30B or the data management server 22.

The sensor direction is detected not according to the verification image but according to the measurement signal. It is possible to detect the sensor direction at the time different from the time of verifying acceptability in the combination between the physiological sensor 11 and the patient P. For example, the problem can be coped with assuming that the physiological sensor 11 is accidentally set in an opposite sensor direction with 180 degrees at a time point after a start of the measurement.

[Fifth Embodiment]

In FIGS. 36-39, the sensor direction of the physiological sensor is detected by the direction detector 91 in the same manner as the fourth embodiment. However, groups of positive and negative electrodes are incorporated in the physiological sensor in association with plural sensor directions instead of the use of correction of the measurement signal. A suitable one of the groups of the electrodes in association with the sensor direction detected by the direction detector 91 is selected to activate the physiological sensor.

Figure 36:
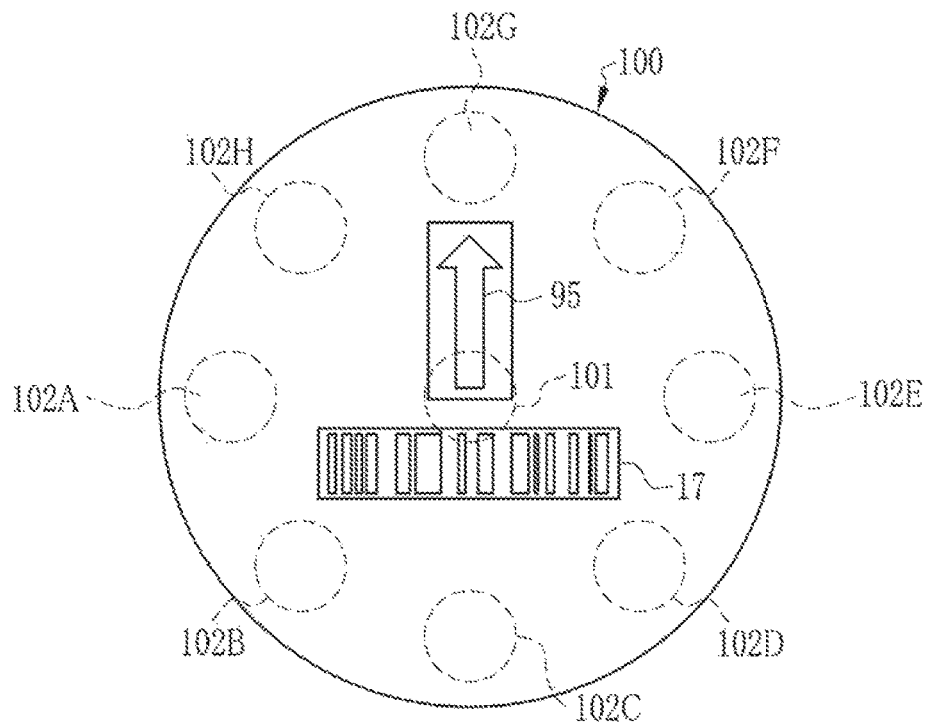
FIG. 36 is a front elevation illustrating the physiological sensor in which pairs of electrodes are indicated.
Figure 37:
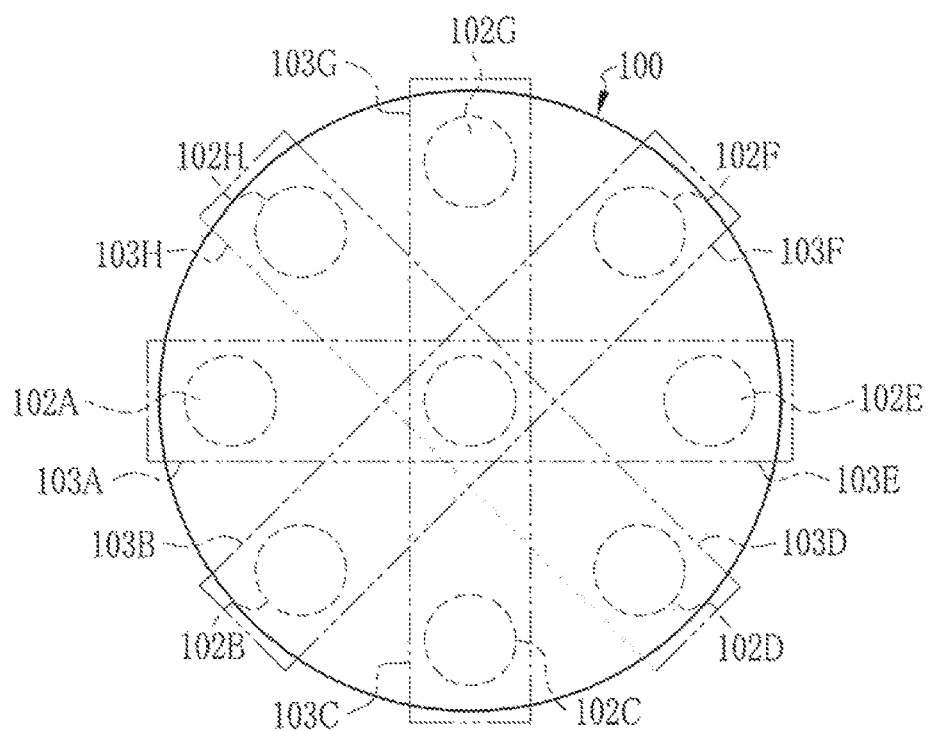
FIG. 37 is a front elevation illustrating the physiological sensor.

In FIGS. 36 and 37, a physiological sensor 100 or ECG sensor (physiological monitoring device) has a structure of a circular shape, and includes a common electrode 101 at the center, and eight particular electrodes 102A, 102B, 102C, 102D, 102E, 102F, 102G and 102H arranged about the common electrode 101 with a regular interval of 45 degrees.

The common electrode 101 is always driven. In contrast, only one of the particular electrodes 102A-102H is selectively driven. A first one of the common electrode 101 and the particular electrodes 102A-102H is positive, and a remaining one of those is negative. The physiological sensor 100 includes an electrode pair 103A. The electrode pair 103A has the common electrode 101 and the particular electrode 102A. Also, the physiological sensor 100 includes electrode pairs 103B, 103C, 103D, 103E, 103F, 103G and 103H. The electrode pair 103B has the common electrode 101 and the particular electrode 102B. The electrode pair 103C has the common electrode 101 and the particular electrode 102C. The electrode pair 103D has the common electrode 101 and the particular electrode 102D. The electrode pair 103E has the common electrode 101 and the particular electrode 102E. The electrode pair 103F has the common electrode 101 and the particular electrode 102F. The electrode pair 103G has the common electrode 101 and the particular electrode 102G. The electrode pair 103H has the common electrode 101 and the particular electrode 102H. In FIG. 37, the bar code 17 and the direction indicator 95 are not shown for simplicity in the depiction.

Figure 38:
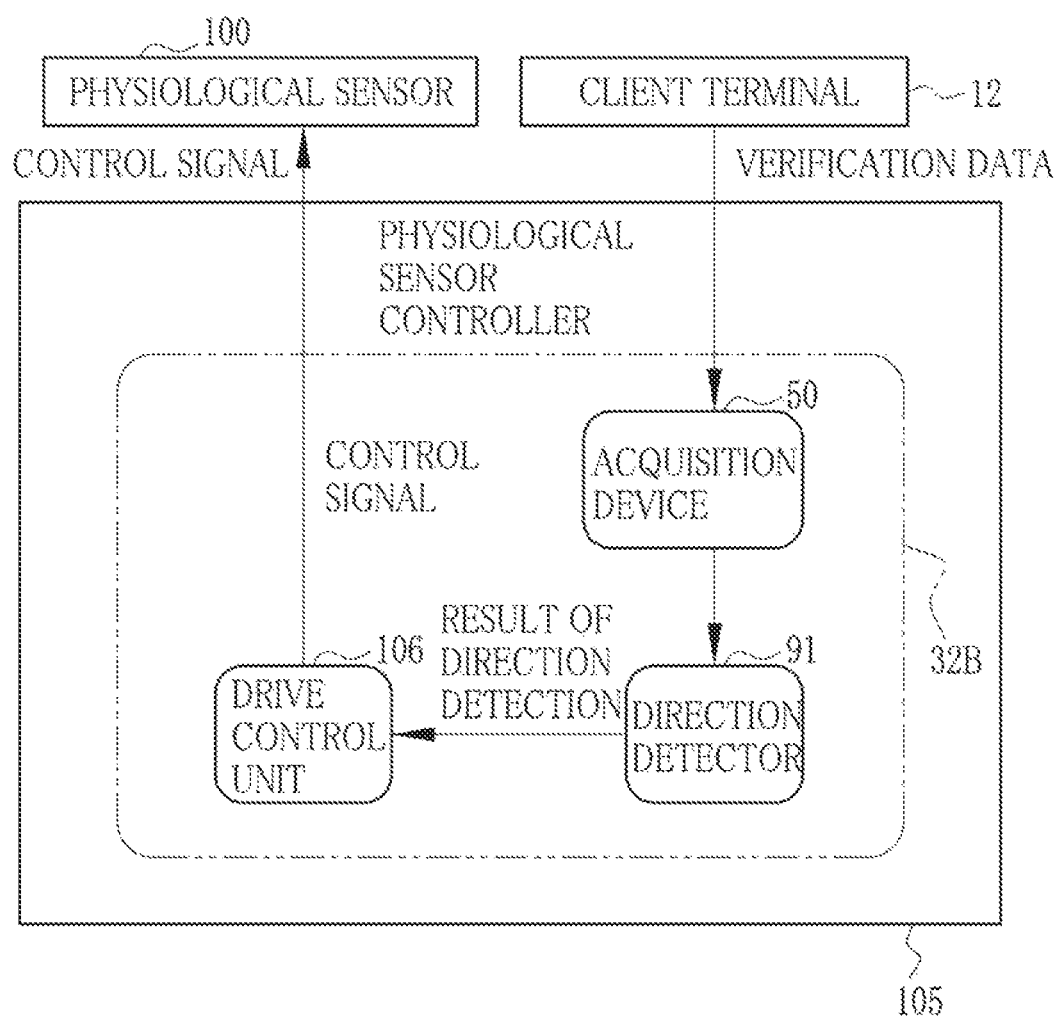
FIG. 38 is a block diagram schematically illustrating circuit devices in a physiological sensor controller.

In FIG. 38, a physiological sensor controller 105 (physiological monitoring apparatus) is illustrated, in which a drive control unit 106 is established in the CPU 32B in addition to the circuit devices 50-56 of the first embodiment and the direction detector 91 of the fourth embodiment. The circuit devices 51-56 are not shown in the drawing of the embodiment.

The drive control unit 106 outputs a control signal to the physiological sensor 100 in correspondence with the result information of the direction detection from the direction detector 91. The control signal is to designate one selected electrode to be driven among the particular electrodes 102A-102H in the physiological sensor 100. The physiological sensor 100 receives the control signal, and drives the selected electrode according to the received control signal.

In FIG. 39, the control signals are indicated in a table for correlation with the pattern (example arrangement) of the center line CL with the direction indicator 95 and the angle defined between the direction indicator 95 and the center line CL. A hatched portion in a depicted area of the physiological sensor 100 denotes a particular electrode to be driven. For example, the direction indicator 95 and the center line CL are in the pattern A (example arrangement A) and the angle is zero (0) degree. Then the control signal is for driving the particular electrode 102A selectively, namely to select the electrode pair 103A. A control signal at the time of a pattern C (example arrangement C) with a phase difference of 90 degrees of the physiological sensor 100 from the state of the pattern A is for driving the particular electrode 102C selectively, namely to select the electrode pair 103C. In short, the control signal is in such a form that a direction of the electrode pair relative to the center line CL is equal to that at the time of zero (0) degree for the angle. The control signal causes the physiological sensor 100 to operate by selecting a suitable electrode pair corresponding to the sensor direction detected by the direction detector 91.

Consequently, the measurement signal can be equally obtained irrespective of the sensor direction, as the physiological sensor 100 is functioned by selecting a suitable pair among the electrode pairs 103A-103H in association with the particular sensor direction detected by the direction detector 91. It is possible for the patient P easily to position the physiological sensor 100 without paying close attention to the sensor direction.

Furthermore, it is possible to utilize the bar code 17 for the direction indicator 95 in the fourth and fifth embodiments.

[Sixth Embodiment]

In the above embodiment, the message for encouraging the start of the measurement with the physiological sensor 11 is displayed. However, unwanted incidents after the verification are likely to cause failure in receiving the measurement signal in the receiver 52 due to no start of measurement, for example, assuming that the patient P has forgotten inadvertently to turn on the power supply of the physiological sensor 11, or assuming that the battery has been used up.

Figure 40:
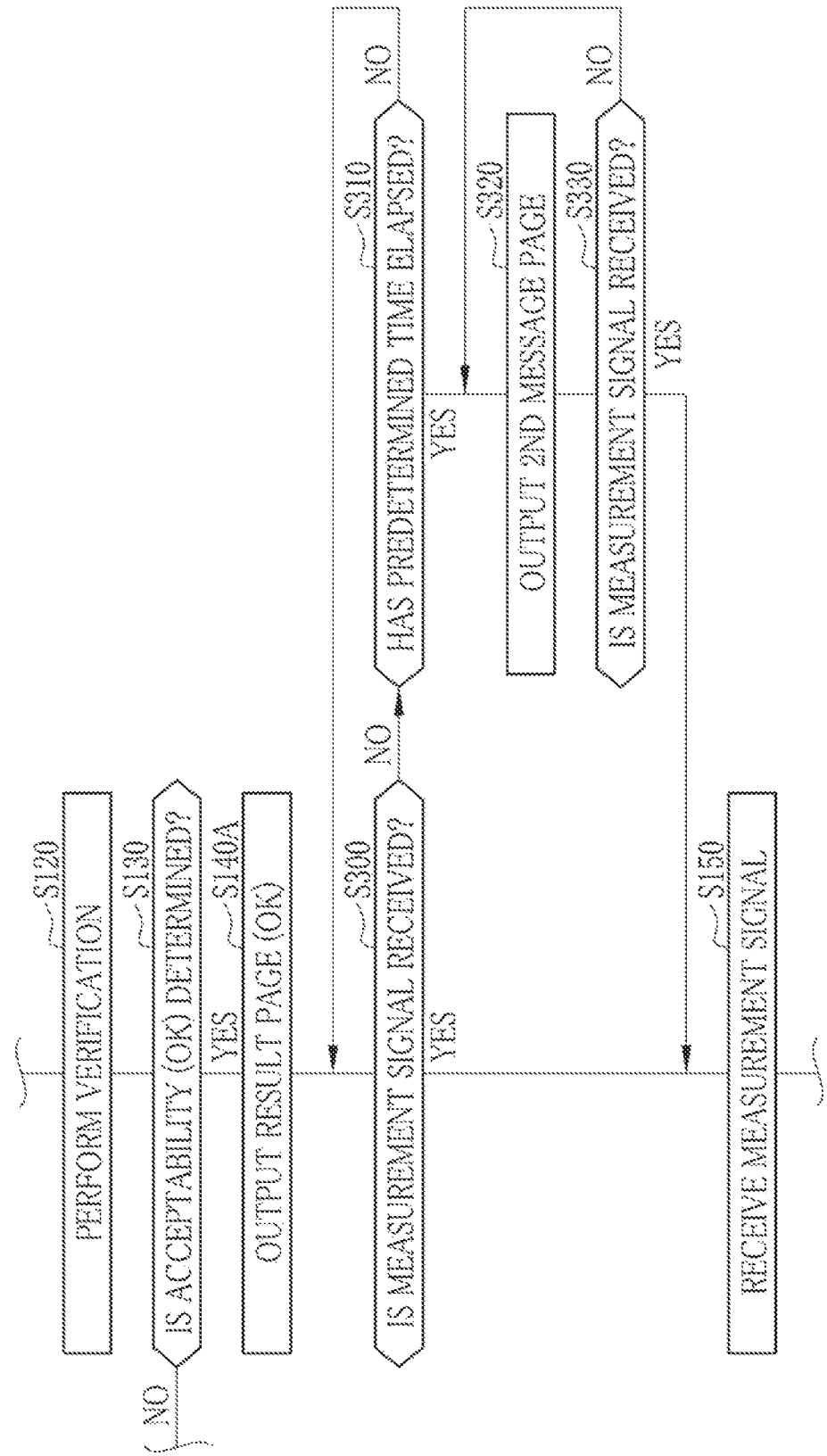
FIG. 40 is a flow chart illustrating control in a sixth preferred physiological sensor controller.
Figure 41:
FIG. 41 is a screen view illustrating a second message page.

In the sixth embodiment, assuming that no measurement signal is received by the receiver 52 even upon lapse of predetermined time after determining correctness of the combination between the physiological sensor 11 and the patient P (examinee) in the verifier 51, the output device 55 according to FIGS. 40 and 41 outputs a message to the client terminal device 12 for encouraging maintenance access to the physiological sensor 11 to resume generation of a measurement signal.

In FIG. 40, the detector 53 checks whether the receiver 52 has received the measurement signal or not in a step S300, after the output device 55 outputs the result page 70A to the client terminal device 12 according to the result of the acceptability (OK) in the verification in the step S140A. Assuming that a non-receptive state of the measurement signal in the receiver 52 continues for the predetermined period (no in the step S300 and yes in a step S310), then a second message page 110 in FIG. 41 is output by the output device 55 to the client terminal device 12 in a step S320, as notification to encourage maintenance access to the physiological sensor 11 to resume generation of the measurement signal. Outputting the second message page 110 is continued until the receiver 52 receives the measurement signal (yes in a step S330).

In FIG. 41, the second message page 110 indicates a message of the non-receptive state of the measurement signal and a message of encouragement of turning on the power of the physiological sensor 11 and exchanging a battery in order to resume outputting a measurement signal from the physiological sensor 11. The second message page 110 is turned off in case the receiver 52 receives a measurement signal after the patient P upon reading the message performs the maintenance access to resume outputting a measurement signal from the physiological sensor 11.

The message for encouraging maintenance access to the physiological sensor 11 to resume outputting a measurement signal is output assuming that no measurement signal is received even upon lapse of predetermined time after verification of correctness in the combination of the physiological sensor 11 with the patient P. It is possible to prevent a problem of failure in receiving the measurement signal in the receiver 52 due to failure in starting the measurement after performing the verification.

[Seventh Embodiment]

Among plural problems of failure of starting the measurement after performing the verification, use of a new battery with sufficient power in connection with the physiological sensor 11 can remove a problem of use-up of the power of the battery at the physiological sensor 11 in an earlier step of distributing the physiological sensor 11 to the patient P in the medical facility 15. However, it is impossible in the medical facility 15 to prevent a problem of inadvertent turn-off of the power source for the physiological sensor 11 in relation to the awareness of the patient P.

Figure 42:
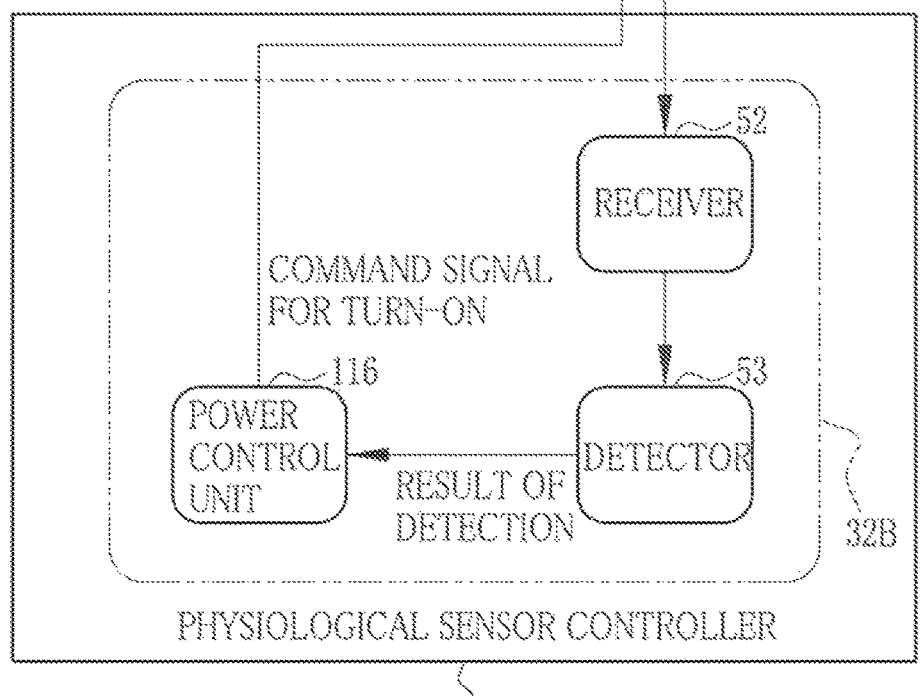
FIG. 42 is a block diagram schematically illustrating circuit devices in a seventh preferred physiological sensor controller.

In FIG. 42, a seventh preferred embodiment is illustrated. Assuming that no measurement signal is received by the receiver 52 and assuming that the power supply for the physiological sensor 11 is turned off even upon the lapse of a predetermined time after determining the correctness in the combination between the physiological sensor 11 and the patient P in the verifier 51, then turn-on of the power supply for the physiological sensor 11 is instructed.

In FIG. 42, a power control unit 116 is established in the CPU 32B of a physiological sensor controller 115 (physiological monitoring apparatus) in addition to the circuit devices 50-56 of the first embodiment. The acquisition device 50, the verifier 51 and the circuit devices 54-56 are not shown. Even while the power supply for the physiological sensor 11 is turned off, a communication path between the physiological sensor 11 and the physiological sensor controller 115 is established. A turn-on state or turn-off state of the power supply for the physiological sensor 11 is always monitored by the physiological sensor controller 115.

In a manner similar to the sixth embodiment, the detector 53 checks whether the receiver 52 receives the measurement signal after the output device 55 outputs the result page 70A to the client terminal device 12 with the result information of acceptability of the verification. Assuming that a non-receptive state of the measurement signal is continued for a predetermined time in the receiver 52 and assuming that the power supply for the physiological sensor 11 is turned off, then the power control unit 116 outputs a command signal to the physiological sensor 11 for turning on the power supply. The physiological sensor 11 receives the command signal, so that the power supply is turned on, to start outputting the measurement signal.

Assuming that a condition without receiving the measurement signal in the receiver 52 is continued for predetermined time, and assuming that a power source for the physiological sensor 11 is turned on, then the situation is caused with a reason other than forgetting turn-on of the power source on the side of the patient P. Then the feature of the sixth embodiment is used, to output the second message page 110 from the output device 55 to the client terminal device 12.

Assuming that no measurement signal is received even upon the lapse of the predetermined time after determining correctness in the combination of the physiological sensor 11 and the patient P, and assuming that the power supply for the physiological sensor 11 is turned off, then turn-on of the power supply for the physiological sensor 11 is instructed. It is possible to prevent a problem of a non-receptive state of the measurement signal in the receiver 52 because the patient P has forgotten to turn on the power source and causes failure in starting the measurement even after the verification. It is possible for the patient P easily to handle the power supply for the physiological sensor 11, as the patient P does not require paying close attention in operating the power supply.

Figure 43:
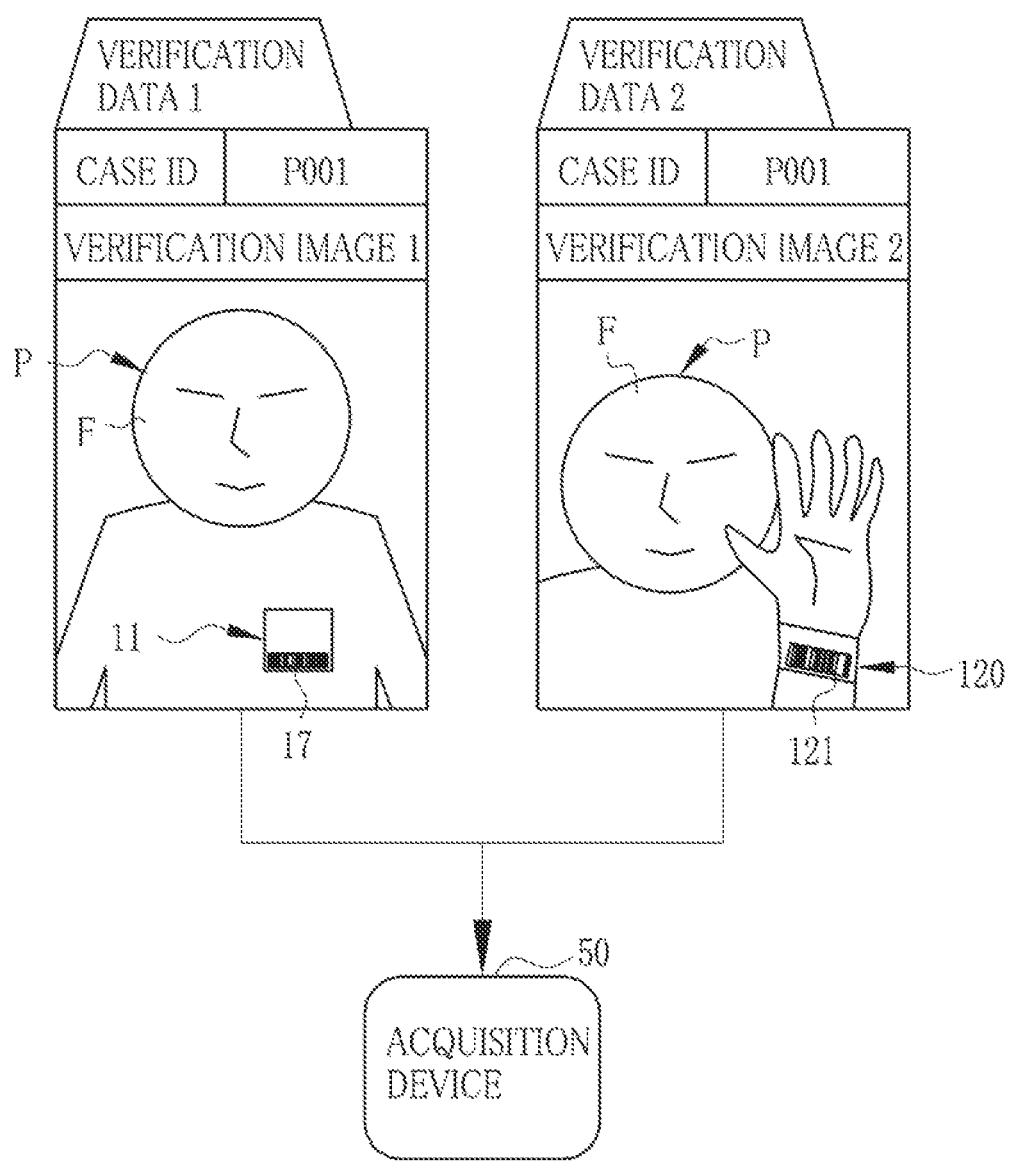
FIG. 43 is a data chart illustrating acquisition of plural image frames for the verification image.

In the above embodiments, the single physiological sensor 11 is positioned on the single patient P. However, two or more of the physiological sensors 11 can be positioned on the patient P. In FIG. 43, a plurality of frames of the verification image for use in verification of one time can be retrieved by the acquisition device 50.

In FIG. 43, verification image 1 of verification data 1 contains an image of the face F of the patient P and the bar code 17 denoting the sensor ID of the physiological sensor 11, in the same manner as the above embodiments. In contrast, verification image 2 of verification data 2 contains an image of the face F of the patient P and a bar code 121 denoting the sensor ID of a physiological sensor 120 or ECG sensor (physiological monitoring device), which is a type different from the physiological sensor 11 and in a form of a wrist band wound around a wrist. For this construction, registration data are prepared in correspondence with the verification data 1 and 2, for which the verifier 51 performs the verification.

In short, the plural frames of the verification images (identification images) for use in verification at one time are acquired. The feature of the invention can be used for the patient P with whom a plurality of physiological sensors are positioned in a wide area which cannot be imaged at one time in a still image. Furthermore, a moving image can be formed instead of the still image. Two or more frames of the moving image can be acquired as verification images.

The physiological sensor can be a device for measuring physiological information, such as a body temperature, blood pressure, heart rate, respiratory rate, skin impedance and the like. Also, plural values of the physiological information can be measured together in one device. An example of the client terminal device may be a notebook type of a personal computer or other portable terminal device in place of the smart phone of the above embodiments, and also can be a device specialized for use for the physiological sensor system. A camera for forming the verification image can be discrete from the client terminal device in contrast with the integrated form in the above embodiments. Furthermore, the camera can be installed in a suitable place in the home 14 of the patient P, for example, a dressing room, so as to form the verification image for automatically in performing verification.

Hardware construction of the computer for constituting the physiological sensor controller of the present invention can be modified suitably. For example, the physiological sensor controller can be constituted by a plurality of computer apparatuses discrete from one another for the purpose of increasing performance of processing and reliability. Specifically, a first computer apparatus may constitute the acquisition device 50, the verifier 51 and the output device 55. A second computer apparatus may constitute the receiver 52, the detector 53 and the checker 54. A third computer apparatus may constitute the data control unit 56. The physiological sensor controller can be constituted by the three computer apparatuses.

In the above embodiments, the verification page 60, the first message page 75 and the like are output by the output device 55 to the client terminal device 12. However, an application program can be installed in the client terminal device 12 for displaying the verification page 60, the first message page 75 and the like. It is possible for the output device 55 to output a command signal for display processing of displaying the verification page 60, the first message page 75 and the like with the client terminal device 12. Note that outputting the command signal for displaying the first message page 75 and the message voice 77 corresponds to outputting a message to the patient P for encouraging a retry for verification.

Figure 44:
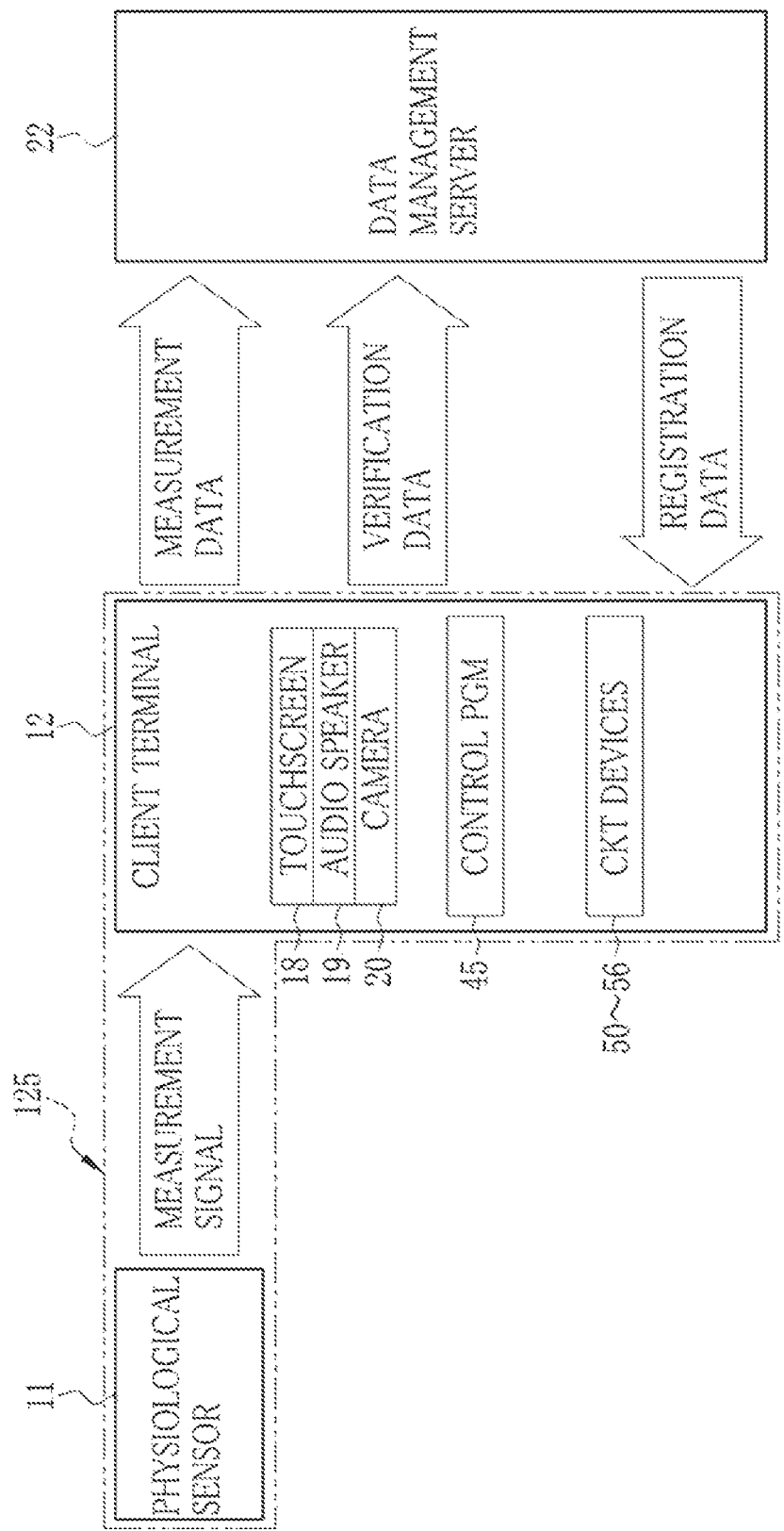
FIG. 44 is a block diagram schematically illustrating a preferred physiological sensor system in which a client terminal device is a physiological sensor controller.
Figure 45:
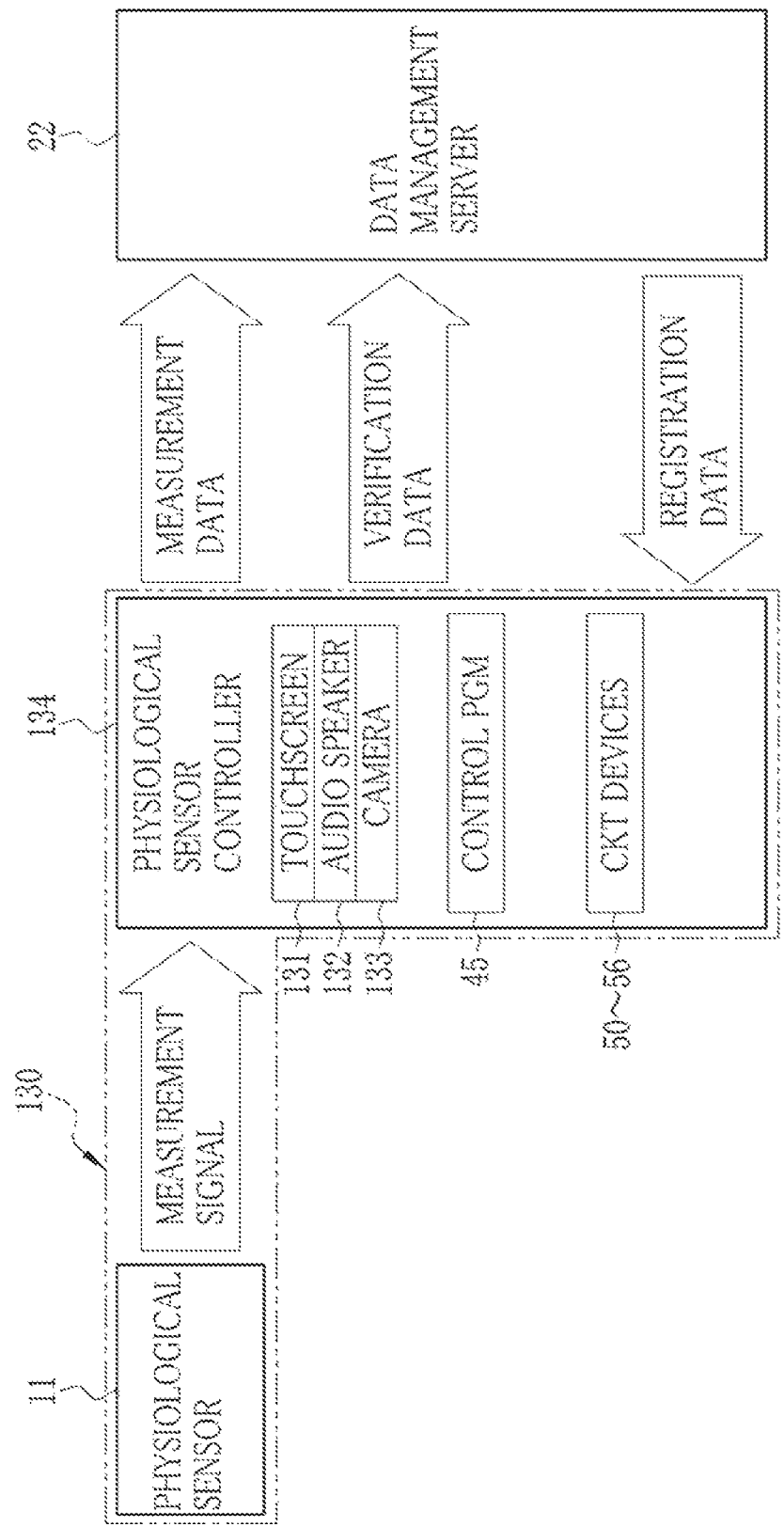
FIG. 45 is a block diagram schematically illustrating a preferred physiological sensor system in which a physiological sensor controller has a display panel.

In FIG. 44, another preferred physiological sensor system 125 (patient monitoring system) is illustrated. The control program 45 is installed in the client terminal device 12, which can be operated as a physiological sensor controller by establishing the circuit devices 50-56 in the client terminal device 12. In FIG. 45, still another preferred physiological sensor system 130 (patient monitoring system) does not have the client terminal device 12. A physiological sensor controller 134 (physiological monitoring apparatus) in the physiological sensor system 130 is constructed to have a touchscreen device 131, an audio speaker 132 and a camera 133 in the same manner as the client terminal device 12. The physiological sensor controller 134 is a specialized component apparatus included in the physiological sensor system 130.

Figure 46:
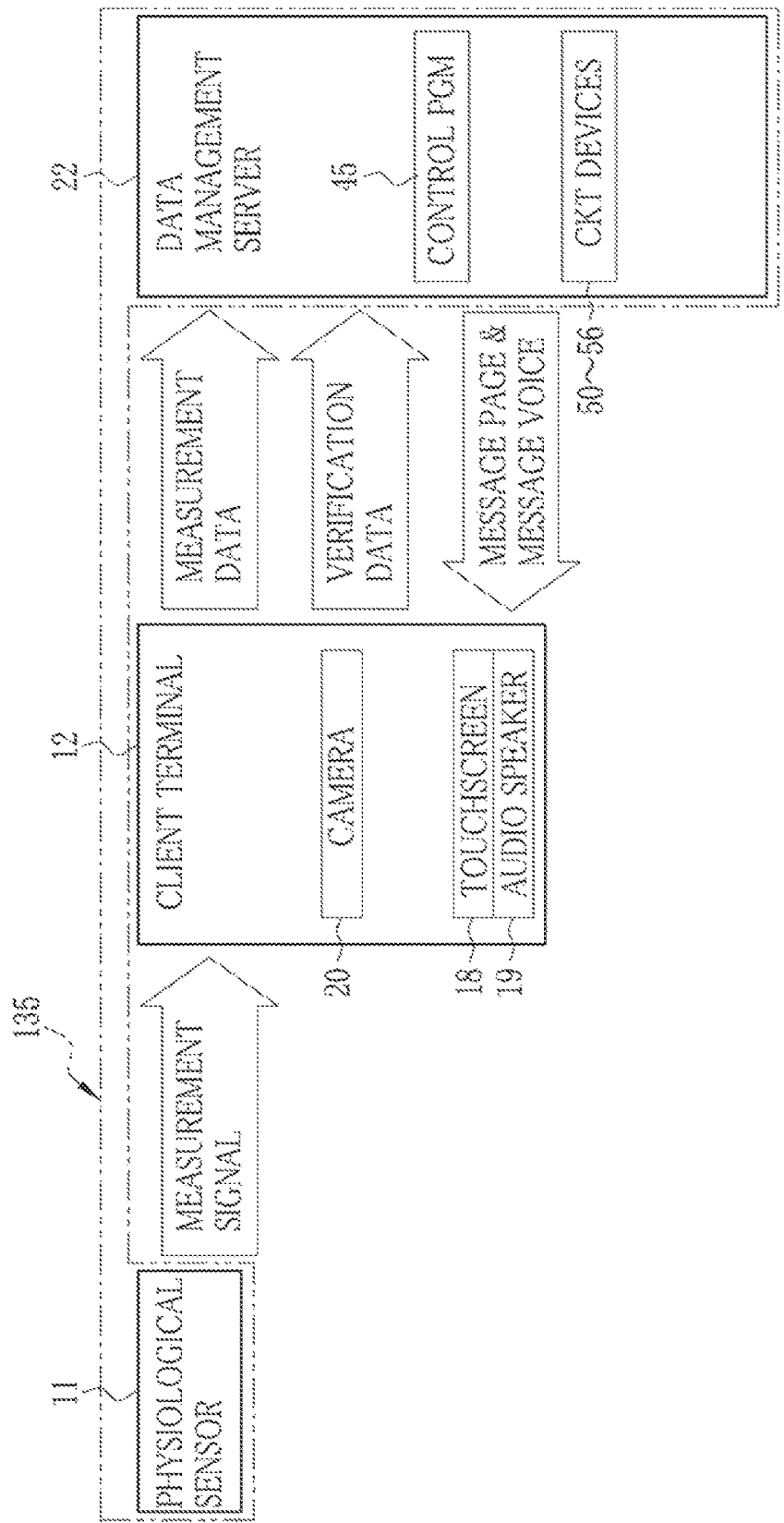
FIG. 46 is a block diagram schematically illustrating a preferred physiological sensor system in which a data management server is a physiological sensor controller.

In FIG. 46, another preferred physiological sensor system 135 (patient monitoring system) is illustrated. The data management server 22 can function as a physiological sensor controller. Furthermore, a physiological sensor controller can be disposed in the medical facility 15 in a manner discrete from the data management server 22.

Thus, the construction of the hardware in the computer can be changed suitably according to performance requiring ability for processing, safety, reliability and the like. Additionally, it is also possible to store the control program 45 and other application programs in a duplicated form or divided form in plural storage media for the purpose of ensuring the safety and the reliability.

The present invention is not limited to the above embodiments. Various features of the embodiments and variants of the invention can be combined with each other suitably. Also, the computer-executable program and a non-transitory computer readable medium for storing the computer-executable program are included in the scope of the present invention.

In a preferred embodiment mode of the invention, a control method of controlling a physiological sensor, positioned on a patient body, for measuring physiological information of the patient body to output a measurement signal, is provided. The control method includes a step of acquiring a verification image containing portions of identification information of the physiological sensor and a face of the patient body. Verification of acceptability in a combination of the physiological sensor and the patient body is performed according to the verification image. The measurement signal is received. Normality or abnormality of receptivity of the measurement signal received by the receiving step is detected. Assuming that the detecting step determines the abnormality of the receptivity, it is checked whether a retry for the verification in the verification step is required or not. Assuming that the checking step determines requirement of the retry for the verification, information of encouraging the retry for the verification is output.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A physiological sensor controller for controlling a physiological sensor, positioned on a patient body, for measuring physiological information of said patient body to output a measurement signal, comprising:
    a processor configured to:
        acquire a verification image containing portions of identification information of said physiological sensor and a face of said patient body;
        perform verification of acceptability in a combination of said physiological sensor and said patient body according to said verification image;
        receive said measurement signal;
        detect normality or abnormality of receptivity of said measurement signal, wherein the abnormality is detected in a case where the measurement signal discontinues for a first predetermined time, or a signal level of the measurement signal continues not to be within a predetermined range for a second predetermined time;
        operate assuming that said processor determines said abnormality of said receptivity, and check whether a retry for said verification is required or not;
        operate assuming that said processor determines requirement of said retry for said verification, and output information of encouraging said retry for said verification, in a visible or audible form,
    wherein said processor is further configured to determine that said retry for said verification is required in a case where a time duration of continuing a state of detecting said abnormality of said receptivity becomes more than a reference time which is longer than the first predetermined time or the second predetermined time.

2. A physiological sensor controller as defined in claim 1, wherein said checker checks whether said retry for said verification is required according to a result of comparison between a measurement signal before detecting said abnormality of said receptivity and a measurement signal after recovery to said normality of said receptivity.

3. A physiological sensor controller as defined in claim 1, wherein the processor is further configured to detect a sensor position of said physiological sensor according to said verification image;
    wherein assuming that said sensor position detected by said processor is incorrect, said processor outputs information of incorrectness of said sensor position.

4. A physiological sensor controller as defined in claim 3, wherein said information of said incorrectness of said sensor position includes information for guiding to said sensor position being correct.

5. A physiological sensor controller as defined in claim 3, wherein said processor is further configured to detect said sensor position according to a position relationship with a particular body part of said patient body in a portion of said verification image.

6. A physiological sensor controller as defined in claim 1, wherein the processor is further configured to detect a sensor direction of said physiological sensor.

7. A physiological sensor controller as defined in claim 6, wherein said physiological sensor includes a direction indicator for indicating said sensor direction;
    said processor is further configured to acquire said verification image containing a portion of said direction indicator; and
    said processor is further configured to detect said sensor direction according to said verification image.

8. A physiological sensor controller as defined in claim 6, wherein said processor is further configured to detect said sensor direction according to said measurement signal.

9. A physiological sensor controller as defined in claim 6, wherein said processor is further configured to operate assuming that said sensor direction is not determined to be normal, and correct said measurement signal to a measurement signal in a state of normality of said sensor direction.

10. A physiological sensor controller as defined in claim 6, wherein said physiological sensor includes pairs of positive and negative electrodes corresponding to plural sensor directions;
    wherein said processor is further configured to activate said physiological sensor by selecting a suitable pair of positive and negative electrodes among said pairs according to said sensor direction detected.

11. A physiological sensor controller as defined in claim 1, wherein assuming that said processor does not receive said measurement signal upon lapse of predetermined time after said processor determines said acceptability in said combination, then said processor provides notification that maintenance access to said physiological sensor should be performed to resume outputting said measurement signal.

12. A physiological sensor controller as defined in claim 1, wherein the processor is further configured to operate assuming that said processor does not receive said measurement signal upon lapse of predetermined time after said processor determines said acceptability in said combination, and assuming that a power supply for said physiological sensor is turned off, and cause turn-on of said power supply in relation to said physiological sensor.

13. A physiological sensor controller as defined in claim 1, wherein said processor is further configured to acquire plural image frames of said verification image for use in one time of said verification.

14. A non-transitory computer readable medium for storing a computer-executable program enabling execution of computer instructions to perform operations for controlling a physiological sensor, positioned on a patient body, for measuring physiological information of said patient body to output a measurement signal, said operations comprising:
    acquiring a verification image containing portions of identification information of said physiological sensor and a face of said patient body;

performing verification of acceptability in a combination of said physiological sensor and said patient body according to said verification image;

receiving said measurement signal;

detecting normality or abnormality of receptivity of said measurement signal received by said receiving operation, wherein the abnormality is detected in a case where the measurement signal discontinues for a first predetermined time, or a signal level of the measurement signal continues not to be within a predetermined range for a second predetermined time;

assuming that said detecting operation determines said abnormality of said receptivity, checking whether a retry for said verification in said verification operation is required or not;

assuming that said checking operation determines requirement of said retry for said verification, outputting information of encouraging said retry for said verification, in a visible or audible form, wherein said retry for said verification is required is determined in a case where a time duration of continuing a state of detecting said abnormality of said receptivity becomes more than a reference time which is longer than the first predetermined time or the second predetermined time.

15. A physiological sensor system, including a physiological sensor, positioned on a patient body, for measuring physiological information of said patient body to output a measurement signal, and a physiological sensor controller for controlling said physiological sensor, comprising:

said physiological sensor controller including:

a processor configured to:

acquire a verification image containing portions of identification information of said physiological sensor and a face of said patient body;

perform verification of acceptability in a combination of said physiological sensor and said patient body according to said verification image;

receive said measurement signal;

detect normality or abnormality of receptivity of said measurement signal, wherein the abnormality is detected in a case where the measurement signal discontinues for a first predetermined time, or a signal level of the measurement signal continues not to be within a predetermined range for a second predetermined time;

operate assuming that said processor determines said abnormality of said receptivity, and check whether a retry for said verification is required or not;

operate assuming that said processor determines requirement of said retry for said verification, and output information of encouraging said retry for said verification, in a visible or audible form, wherein said processor is further configured to determine that said retry for said verification is required in a case where a time duration of continuing a state of detecting said abnormality of said receptivity becomes more than a reference time which is longer than the first predetermined time or the second predetermined time.

16. The physiological sensor controller as defined in claim 1, wherein the first predetermined time and the second predetermined time are 5-10 times as long as a sampling period of the measurement signal.

17. The physiological sensor controller as defined in claim 1, wherein the first predetermined time and the second predetermined time are from several milliseconds to several tens of milliseconds, and the reference time is from several seconds to several tens of seconds.

* * * * *